US010980847B2

(12) United States Patent
Urban et al.

(10) Patent No.: US 10,980,847 B2
(45) Date of Patent: Apr. 20, 2021

(54) COMPOSITIONS AND METHODS FOR DETECTING AND TREATING BRAIN INJURY ASSOCIATED FATIGUE AND ALTERED COGNITION (BIAFAC)

(71) Applicant: BOARD OF REGENTS, THE UNIVERSITY OF TEXAS SYSTEM, Austin, TX (US)

(72) Inventors: Randall J. Urban, Friendswood, TX (US); Melinda Sheffield-Moore, College Station, TX (US); Richard Pyles, Galveston, TX (US); Brent Masel, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/449,047

(22) Filed: Jun. 21, 2019

(65) Prior Publication Data
US 2019/0388482 A1 Dec. 26, 2019

Related U.S. Application Data

(60) Provisional application No. 62/688,106, filed on Jun. 21, 2018.

(51) Int. Cl.
A61K 35/741 (2015.01)
A61K 9/00 (2006.01)
C12Q 1/689 (2018.01)

(52) U.S. Cl.
CPC .......... A61K 35/741 (2013.01); A61K 9/0031 (2013.01); A61K 9/0053 (2013.01); C12Q 1/689 (2013.01)

(58) Field of Classification Search
CPC ........ A61K 6/54; A61K 6/887; A61K 35/741; A61K 2300/00; A61K 2035/115; A61K 35/74; A61K 6/52; A61K 6/69; A61K 9/0031; A61K 9/0053
See application file for complete search history.

(56) References Cited

U.S. PATENT DOCUMENTS 10,111,914 B2 * 10/2018 Bailey ..................... A61P 25/18

OTHER PUBLICATIONS

Arumugam et al., (Nature. May 12, 2011; 473(7346): 174-180). (Year: 2011).*
Lucke et al 2006 Journal of Medical Microbiology, vol. 55, Issue 55, 617-624 (Year: 2006).*
Winter et al., "Gut microbiome and depression: what we know and what we need to know", Rev. Neurosci. 2018; 29(6): 629-643.
Yamamoto et al., "Impact & Blast Traumatic Brain Injury: Implications for Therapy", Molecules, 2018, 23, 245.
Ye, et al., "A Parsimony Approach to Biological Pathway Reconstruction/Inference for Genomes and Metagenomes", PLOS Computational Biology, Aug. 2009, vol. 5, Issue 8.
Yilmaz, P. et al., "The SILVA and "All-species Living Tree Project (LTP)" taxonomic frameworks", Nucleic Acids Research, 2014, vol. 42, Database Issue D643-D648.
Zhu C. et al., "A Review of Traumatic Brain Injury and the Gut Microbiome: Insights into Novel Mechanisms of Secondary Brain Injury and Promising Targets for Neuroprotection", Brian Sciences MDPI, 2018, 8, 113.
Bansal et al., "Stimulating the Central Nervous System to Prevent Intestinal Dysfunction After Traumatic Brain Injury", J. Trauma, May 2010, 68(5) 1059-1064.
Benjamini et al., "Controlling the False Discovery Rate: A Practical and Powerful Approach to Multiple Testing", vol. 57, No. 1, (1995), pp. 289-300. Royal Statistical Society.
Berer et al., "Gut microbiota from multiple sderosis patients enables spontaneous autoimmune encephalomyelitis in mice", PNAS, Oct. 3, 2017, vol. 114, No. 40, 10719-10724.
Blankenberg et al., "Manipulation of FASTQ data with Galaxy", Bioinformatic, vol. 26 No. 14 2010, pp. 1783-1785.
Caporaso et al., "Ultra-high-throughput microbial community analysis on the Illumina HiSeq and MiSeq platforms", The ISME Journal (2012) 6, 1621-1624.
Durham et al., "Hypoaminoacidemia Characterizes Chronic Traumatic Brain In", Journal of Neurotrauma 34:385-390 (Jan. 15, 2017).
Duvallet et al., "Meta-analysis of gut microbiome studies identifies disease-specific and shared responses", Nature Communications, DOI: 10.1038/s41467-017-01973-8.
Edgar, Robert, "Search and clustering orders of magnitude faster than BLAST", Bioinformatics, vol. 26 No. 19 2010, pp. 2460-2461.
Edgar, Robert, "U PARSEARSEARSEARSE: highly accurate OTUOTUOTU sequences from microbial amplicon reads", 996 | vol. 10 No. 10 | Oct. 2013 | nature methods.
Esterov et al., "Autonomic Dysfunction after Mild Traumatic Brain Injury", Brain Sciences, 2017, 7, 100; doi:10.3390/brainsci7080100.
Gill et al., "Metagenomic Analysis of the Human Distal Gut Microbiome", Science, vol. 312, Jun. 2, 2006.
Grimes et al., "Intraluminal Flagellin Differentially Contributes to Gut Dysbiosis and Systemic Inflammation following Burn Injury", PLOS ONE, DOI:10.1371/journal.pone.0166770 Dec. 1, 2016.
Herbeck et al., "Nutritional Features of the Intestinal Anaerobe Ruminococcus bromii", Applied Microbiology, Dec. 1974, p. 1018-1022, vol. 28, No. 6.
Human 2012, "A framework for Human Microbiome Research", DOI: 10/1038/Nature, 11209.

(Continued)

Primary Examiner — Padmavathi Baskar
(74) Attorney, Agent, or Firm — Edwin S. Flores; Chalker Flores, LLP

(57) ABSTRACT

The present invention includes composition, methods and kits for detecting and treating brain injury associated fatigue or altered cognition (BIAFAC) in a human patient comprising: identifying a human patient in need of treatment for brain injury associated fatigue or altered cognition associated with an altered intestinal flora; and providing the human patient with a composition comprising at least one of: a *Prevotella* spp or a *Bacteroidies* spp bacteria, or one or more agents that increase the amount of the *Prevotella* spp or the *Bacteroidies* spp bacteria in an intestinal flora of the human patient to reduce or eliminate the brain injury associated fatigue or altered cognition.

3 Claims, 6 Drawing Sheets

(56) References Cited

OTHER PUBLICATIONS

Human 2012, "Structure, function and diversity of the healthy human microbiome", doi:10.1038/nature11234.
Javurek et al., "Gut Dysbiosis and Neurobehavioral Alterations in Rats Exposed to Silver Nanoparticles", Scientific Reports, 7: 2822, DOI:10.1038/s41598-017-02880-0.
Jiang et al., "Dysbiosis gut microbiota associated with inflammation and impaled mucosal immune function in intestine of humans with non-alcoholic fatty liver disease", Scientific Reports, 5 : 8096, DOI: 10.1038/srep08096.
Katzenberger et al., "The gut reaction to traumatic brain injury", Fly 9:2, 68-74; Apr./May/Jun. 2015; © 2015 Taylor & Francis Group, LLC.
Klindworth et al., "Evaluation of general 16S ribosomal RNA gene PCR primers for classical and next-generation sequencing-based diversity studies", Nucleic Acids Research, 2013, vol. 41, No. 1, doi:10.1093/nar/gks808.
Langmead et al., "Fast gapped-read alignment with Bowtie 2", NIH Public Access, Nat Methods. ; 9(4): 357-359. doi:10.1038/nmeth. 1923.
Larsen, "The immune response to Prevotella bacteria in chronic inflammatory disease", Immunology, 2017 John Wiley & Sons Ltd, Immunology, 151, 363-374.
Lê Cao et al., "A Sparse PLS for Variable Selection when Integrating Omics data", HAL, Archives-Ouvertes, 2008, 7(1), pp. 35. 10.2202/1544-6115.1390. hal-00300204v.
Le Cao et al., "integrOmics: an R package to unravel relationships between two omics datasets", Bioinforrnatics, vol. 25 No. 21 2009, pp. 2855-2856, doi:10.1093/bioinformatics/btp515.
Lozupone et al., "UniFrac: a New Phylogenetic Method for Comparing Microbial Communities", Applied and Environmental Microbiology, Dec. 2005, p. 8228-8235, vol. 71, No. 12.
Martin M., "Cutadapt Removes Adapter Sequences from High-Throughput Sequencing reads", Technical Notes, 2011, EMBnet. Journal 17.1.
Martin C., etal., "Gut-Brain Axis and Behavior", HHS Public Access, Nestle Nutr Inst Workshop Ser. 2017 ; 88: 45-53. doi:10. 1159/000461732.
Mayer, E., "Gut/brain Axis and the Microbiota", JCI, vol. 125, No. 3, Mar. 2015, 925-938.
Miller P. etal., "TNFR2 Deficiency Acts in Concert with Gut Microbiota to Precipitate Spontaneous Sex-Biased Central Nervous System Demyelinating Autoimmune Disease", Oct. 2015; Journal of Immunology, 2015; 195:4668-4684; Prepublished online Oct. 16, 2015.
Morgan, B. Paul etal., "Complement, a target for therapy in inflammatory and degenerative diseases", Nature Reviews Drug Discovery(vol. 14, Issue 12.).
Nagy-Szakal et al. "Fecal metagenomic profiles in subgroups of patients with myalgic encephalomyelitis/chronic fatigue syndrome", Microbiome (2017) 5:44.
Olsen, A.B., et al., "Effects of Traumatic Brain Injury on Intestinal Contractility", Neurogastroenterol Motil (2013) 25, 693-e463.
Paramsothy, S., etal., "Specific Bacteria and Metabolites Associated With Response to Fecal Microbiota Transplantation in Patients With Ulcerative Colitis", Gastroenterology 2019;156:1440-1454.
Pedersen, H.K., et al., "Human gut microbes impact host serum metabolome and insulin sensitivity", Nature , vol. 535, Jul. 21, 2016.
Pianta, A., et al., "Evidence of the Immune Relevance of Prevotella copri, a Gut Microbe, in Patients With Rheumatoid Arthritis", Arthritis & Rheumatology, vol. 69, No. 5, May 2017, pp. 964-975.
Quast, et al., "The SILVA ribosomal RNA gene database project: Improved Data Processing and Web-Based Tools", Nucleic Acids Research, 2013, vol. 41, Database issue.
Rogers, et al., "From Gut Dysbiosis to Altered Brain Function and Mental Illness: Mechanisms and Pathways", Molecular Psychiatry (2016) 21, 738-748.
Roland, et al., "Small Intestinal Transit Time is Delayed in Small Intestinal Bacterial Overgrowth", Clin Gastroenterol, vol. 49, No. 7, Aug. 2015.
Schmieder, et al., "Quality Control and Preprocessing of Metagenomic Datasets", Bioinformatics, vol. 27 No. 6 2011, pp. 863-864.
Smeets. et al., "Do anabolic nutritional supplements stimulate human growth hormone secretion in elderly women with heart failure?", Physiological Reports ISSN 2051-817X, 2017, vol. 5, Iss. 15, pp. 1-7.
Smith, K., "Neurogastroenterology TBI Affects Intestinal Motility", Nature Reviews Gastroenterology & Hepatology, vol. 10., May 2013.
Sun, Meng-Fei et al., "Dysbiosis of gut microbiota and microbial metabolites in Parkinson's Disease", Ageing Research Reviews, 2, 2018.
Sundman, Mark H., et al., "The bidirectional gut-brain-microbiota axis as a potential nexus between tramatic brain injury, inflammation, and disease", Brain, Behavior, and Immunity, 66, 2017, 31-44.
Taylor, C., et al., "Traumatic Brain Injury-Related Emergency Department Visits, Hospitalizations, and Deaths", MMWR, Mar. 17, 2017, Surveillance Summaries, vol. 66, No. 9.
The R Core Team, "R: A Language and Environment for Statistical Computing", Version 3.6.1, Jul. 5, 2019.
Turnbaugh, P. J., et al., "The human microbiome project: exploring the microbial part of ourselves in a changing world", Nature, Oct. 18, 2007, 449(7164), pp. 804-810.

* cited by examiner

COMPOSITIONS AND METHODS FOR DETECTING AND TREATING BRAIN INJURY ASSOCIATED FATIGUE AND ALTERED COGNITION (BIAFAC)

CROSS-REFERENCE TO RELATED APPLICATIONS

This application claims priority to U.S. Provisional Application Ser. No. 62/688,106, filed Jun. 21, 2018, the entire contents of which are incorporated herein by reference.

STATEMENT OF FEDERALLY FUNDED RESEARCH

Not Applicable.

TECHNICAL FIELD OF THE INVENTION

The present invention relates in general to the field of novel compositions and methods for detecting and treating brain injury associated fatigue and altered cognition (BIAFAC).

BACKGROUND OF THE INVENTION

Without limiting the scope of the invention, its background is described in connection with traumatic brain injury and changes in cognition.

Following traumatic brain injury (TBI) or other central nervous system (CNS) maladies (e.g. stroke or hemorrhage), patients develop a clinical syndrome characterized by fatigue, altered cognition, chronic inflammation and altered amino acid absorption. Unfortunately, current treatments for these conditions (referred to herein as brain injury associated fatigue and altered cognition (BIAFAC)) involve daily injection of expensive recombinant human growth hormone that treats the syndrome but does not produce a lasting cure.

Others have attempted to treat TBI or other CNS maladies with varying results. One such patent is International Publication No. WO2017152137 A3, filed by Lynch, et al., entitled "Microbial consortium and uses thereof". These applicants teach microbial compositions and methods of using the same that include therapeutically effective amounts of *Lactobacillus johnsonii, Faecalibacterium prausnitzii, Akkermansia muciniphila, Myxococcus xanthus* and *Pediococcus pentosaceus*, which are said to be particularly useful for methods of treating and preventing inflammatory diseases.

Another such patent is International Publication No. WO2017191638A1, filed by Ilan, entitled "Hyperimmune colostrum in the modulation and treatment of conditions associated with the mammalian microbiome". This inventor is said to teach methods and compositions for modulating, preventing or treating non-clinical and clinical conditions that are associated with a mammalian microbiome. The methods and compositions are said to include preparations of hyperimmune colostrum enriched with antibodies for lipopolysaccharides (anti-LPS) that directly or indirectly impact the mammalian microbiome to alleviate and treat various forms of renal failure, hypertension, heart disease, atherosclerosis and sepsis, and various psychiatric and neurobehavioral conditions.

Another such patent is International Publication No. WO2017181158A1, filed by Costa-Mattioli, et al., entitled "Probiotic therapies for developmental disorders and other neurological disorders". These inventors teach methods and compositions to manipulate the microbiome in an individual having at least one social behavior deficit. More particularly, an individual that has at least one social behavior deficit and was born from a mother who during pregnancy was obese, overweight, or on a high-fat diet during pregnancy or carries mutations associated with neurodevelopmental disorders is provided an effective amount of *Lactobacillus reuteri* for the improvement of at least one symptom of a social behavior deficit.

Finally, another patent is U.S. Patent Publication No. 20120128711, filed by Hausman, et al., that is entitled "Anti-inflammatory approach to prevention and suppression of post-traumatic stress disorder, traumatic brain injury, depression and associated disease states". This application is said to teach composition and methods for the prevention and control of inflammation and oxidative stress and various associated medical conditions, including PTSD, chronic depression and traumatic brain injury. These applicants disclose a composition that includes a phytonutrient and enriched mushrooms having enhanced Vitamin D and ergothioneine. The enriched mushroom and phytonutrient are said to provide a synergistic effect on cellular longevity and/or cellular rejuvenation of subjects with both a normal and nutritionally deficient diets, improved tolerance to oxidative and/or inflammatory stress as a result of the neutralization of free radicals and prevention of chronic inflammation.

However, a need remains for tests and treatments for brain injury associated fatigue and altered cognition resulting for diseases or conditions that cause decreased cognition.

SUMMARY OF THE INVENTION

In one embodiment, the present invention includes a method of treating brain injury associated fatigue or altered cognition (BIAFAC) in a human patient comprising: identifying a human patient in need of treatment for brain injury associated fatigue or altered cognition associated with an altered intestinal flora; and providing the human patient with a composition comprising at least one of: a *Prevotella* spp or a *Bacteroidies* spp bacteria, or one or more agents that increase the amount of the *Prevotella* spp or the *Bacteroidies* spp bacteria in an intestinal flora of the human patient to reduce or eliminate the brain injury associated fatigue or altered cognition. In one aspect, the human patient has brain injury that is chronic, mild, or undiagnosed. In another aspect, the human patient has brain injury caused by stroke, hemorrhage, surgery, or radiation. In another aspect, the composition further comprises an amino acid mixture that promotes the growth of *Prevotella* spp or *Bacteroidies* spp bacteria. In another aspect, the composition further comprises an agent that reduces or eliminates *Ruminococcaceae* genus bacteria. In another aspect, the agent that reduces or eliminates *Ruminococcaceae* genus bacteria is selected from an amino acid mixture, an antibacterial agent, a bacteriophage, or an antimicrobial CRISP-Cas system agent. In another aspect, the human patient did not receive a concurrent antibiotic or a probiotic therapy. In another aspect, the bacteria is listed are responsive in Tables 3, 4, 5 and 6. In another aspect, the method further comprises providing the patient with a fecal transplant comprising *Prevotella* spp or *Bacteroidies* spp bacteria or healthy bacterial community containing *Prevotella* spp or *Bacteroidies* spp. In one aspect, the method further comprises providing the human patient a bacterial composition that is modified to correct a TBI flora to a normal flora is provided before, during, or after undergoing a colon cleanse treatment, delivered by colonoscope, wherein the bacterial composition is not a fecal transplant, or wherein bacteria are lab-grown, or wherein bacteria are lab-grown and customized to specifically modify a TBI flora of a specific patient.

In another embodiment, the present invention includes a method of identifying a patient with a brain injury associated fatigue or altered cognition (BIAFAC) that will benefit from a probiotic bacteria treatment comprising: identifying a human patient with a brain injury associated fatigue or altered cognition; obtaining a biological sample from the patient that comprises gut intestinal flora; and determining whether the gut intestinal flora in the biological sample comprises a decrease in the presence of probiotic bacteria selected from at least one of *Prevotella* spp or *Bacteroidies* spp bacteria, when compared to a normal human sample. In one aspect, the method further comprises treating the subject with a composition comprising one or more probiotic bacteria selected from at least one of: *Prevotella* spp or *Bacteroidies* spp, or one or more agents that increase the amount of *Prevotella* spp or *Bacteroidies* spp in an intestinal flora of the patient, wherein the composition comprises an amount effective to reduce or eliminate the brain injury associated fatigue or altered cognition. In another aspect, the method further comprises providing the patient with a fecal transplant comprising *Prevotella* spp or *Bacteroidies* spp. In another aspect, the biological sample is a fecal sample. In another aspect, the presence of the probiotic bacteria is determined by at least one of metagenomic shotgun sequencing of bacteria, quantitative PCR assays or metabolic LC-MS analysis of bacterial metabolites. In another aspect, the method further comprises the step of providing the patient with an agent that reduces or eliminates *Ruminococcaceae* genus bacteria. In another aspect, the agent that reduces or eliminates *Ruminococcaceae* genus bacteria is selected from an amino acid mixture, an antibacterial agent, a bacteriophage, or an antimicrobial CRISP-Cas system agent. In another aspect, the human patient has brain injury that is chronic, mild, or undiagnosed. In another aspect, the human patient has brain injury caused by stroke, hemorrhage, surgery, or radiation. In another aspect, the composition further comprises an amino acid mixture that promotes the growth of *Prevotella* spp or *Bacteroidies* spp. In another aspect, the composition further comprises an amino acid mixture that reduces or eliminates *Ruminococcaceae* genus bacteria. In another aspect, the patient did not receive a concurrent antibiotic or a probiotic therapy. In another aspect, one or more bacteria for treatments are listed in Tables 3, 4, 5 and/or 6. In another aspect, a bacterial composition that is modified to correct a TBI flora to a normal flora is provided before, during, or after undergoing a colon cleanse treatment, delivered by colonoscope, wherein the bacterial composition is not a fecal transplant, or wherein bacteria are lab-grown, or wherein bacteria are lab-grown and customized to specifically modify a TBI flora of a specific patient.

In another embodiment, the present invention includes a composition for treating brain injury associated fatigue or altered cognition in a human patient comprising one or more probiotic bacteria selected from at least one of: *Prevotella* spp or *Bacteroidies* spp, in an effective amount sufficient to reduce or eliminate the brain injury associated fatigue or altered cognition. In one aspect, the composition further comprises a fecal transplant comprising *Prevotella* spp or *Bacteroidies* spp. In another aspect, the composition further comprises an agent that reduces or eliminates *Ruminococcaceae* genus bacteria. In another aspect, the agent that reduces or eliminates *Ruminococcaceae* genus bacteria is selected from an amino acid mixture, an antibacterial agent, a bacteriophage, or an antimicrobial CRISP-Cas system agent. In another aspect, the composition further comprises an amino acid mixture that promotes the growth of *Prevotella* spp or *Bacteroidies* spp. In another aspect, the patient did not receive a concurrent antibiotic or a probiotic therapy. In another aspect, one or more bacteria for treatments are listed in Tables 3, 4, 5 and/or 6. In another aspect, a bacterial composition that is modified to correct a TBI flora to a normal flora is provided before, during, or after undergoing a colon cleanse treatment, delivered by colonoscope, wherein the bacterial composition is not a fecal transplant, or wherein bacteria are lab-grown, or wherein bacteria are lab-grown and customized to specifically modify a TBI flora of a specific patient.

In another embodiment, the present invention includes a blood test assay that determines a biological profile associated with a bacterial flora that exacerbates a brain injury associated fatigue or altered cognition for testing a fecal sample from a patient that compares the biological profile from a patient to a database of a normal biological profile, wherein the bacterial flora detected is selected from *Prevotella* spp, *Bacteroidies* sp, or *Ruminococcaceae* genus bacteria. In one aspect, the biological profile is further defined as comprising an array that specifically tests for an amino acid profile associated with the presence, absence, or amount of the *Prevotella* spp, *Bacteroidies* sp, or *Ruminococcaceae* genus bacteria. In another aspect, the biological profile is further defined as comprising an array that specifically tests for a nucleic acid profile associated with the presence, absence, or amount of the *Prevotella* spp, *Bacteroidies* sp, or *Ruminococcaceae* genus bacteria. In another aspect, the patient did not receive a concurrent antibiotic or a probiotic therapy. In another aspect, one or more bacteria are listed in Tables 3, 4, 5 and/or 6.

In another embodiment, the present invention includes a kit for screening a patient for a brain injury associated fatigue or altered cognition and choosing a proper treatment based on the screening, the kit comprising: a screening tool that screens the patient for a risk of brain injury associated fatigue or altered cognition, the screening tool comprising a questionnaire and further comprising a screening score system that determines the risk of the patient based on a cumulative point total from answers to the questionnaire; a diagnostic test that categorizes the brain injury associated fatigue or altered cognition based on the cumulative point total from the questionnaire; a fecal sample collection container for determining a bacterial flora in a fecal sample of the patient; instructions for implementing the brain injury associated fatigue or altered cognition treatment; and a brain injury associated fatigue or altered cognition treatment composition comprising one or more probiotic bacteria selected from at least one of: *Prevotella* spp or *Bacteroidies* spp, or one or more agents that increase the amount of *Prevotella* spp or *Bacteroidies* spp in an intestinal flora of the patient, wherein the composition comprises an amount effective to reduce or eliminate the brain injury associated fatigue or altered cognition. In one aspect, the bacterial flora detected is a presence or an amount of a *Prevotella* spp, *Bacteroidies* spp or *Ruminococcaceae* genus bacteria in the fecal sample. In another aspect, the kit comprises a container with reagents for detecting at a genus or species level the bacterial flora selected from at least one of Ion Torrent Personal Genome Machine (PGM), next-generation sequencing (NGS), or qualitative Polymerase Chain Reaction (qPCR). In another aspect, the brain injury associated fatigue or altered cognition treatment is a probiotic therapy regime of the patient based the patient's brain injury associated fatigue or altered cognition. In another aspect, the probiotic therapy regime further comprises one or more agents that reduces or eliminates *Ruminococcaceae* genus bacteria. In another aspect, the human patient has a brain injury that is chronic, mild, undiagnosed. In another aspect, the human patient has a brain injury caused by stroke, hemorrhage, surgery, or radiation. In another aspect, the composition further comprises a fecal transplant comprising *Prevotella* spp or *Bacteroidies* spp. In another aspect, the composition further comprises an amino acid mixture that promotes the growth of *Prevotella* spp or *Bacteroidies* spp. In another aspect, the composition further comprises an amino acid mixture that reduces or eliminates *Ruminococcaceae* genus bacteria. In another aspect, the composition further comprises an agent that reduces or eliminates *Ruminococcaceae* genus bacteria. In another aspect, the agent that reduces or eliminates *Ruminococcaceae* genus bacteria is selected from an antibacterial agent, a bacteriophage, an antimicrobial CRISP-Cas system agent. In another aspect, the patient did not receive a concurrent antibiotic or a probiotic therapy. In another aspect, one or more bacteria for treatments are listed in Tables 3, 4, 5 and/or 6. In another aspect, a bacterial composition that is modified to correct a TBI flora to a normal flora is provided before, during, or after undergoing a colon cleanse treatment, delivered by colonoscope, wherein the bacterial composition is not a fecal transplant, or wherein bacteria are lab-grown, or wherein bacteria are lab-grown and customized to specifically modify a TBI flora of a specific patient.

In another embodiment, the present invention includes a method of diagnosing and treating a patient for brain injury associated fatigue or altered cognition, the method comprising: using an algorithm implemented in a computer program to: screen a patient for a brain injury associated fatigue or altered cognition risk by scoring a questionnaire based on answers from the patient to the questionnaire, the scoring providing a cumulative point total, and determining the brain injury associated fatigue or altered cognition of the patient based on the cumulative point total from the questionnaire; and choosing a proper brain injury associated fatigue or altered cognition treatment product if the brain injury associated fatigue or altered cognition risk exceeds a threshold, the brain injury associated fatigue or altered cognition treatment product comprising a composition comprising one or more probiotic bacteria selected from at least one of: *Prevotella* spp or *Bacteroidies* spp, or one or more agents that increase the amount of *Prevotella* spp or *Bacteroidies* spp in an intestinal flora of the patient, wherein the composition comprises an amount effective to reduce or eliminate the brain injury associated fatigue or altered cognition. In another aspect, the patient preparation instructions include following dietary modifications in accordance with brain injury associated fatigue or altered cognition treatment specifications to at least one of: increase the amount of *Prevotella* spp or *Bacteroidies* spp in the intestinal flora of the patient, or reduces or eliminates *Ruminococcaceae* genus bacteria in the intestinal flora of the patient. In another aspect, the patient did not receive a concurrent antibiotic or a probiotic therapy. In another aspect, one or more bacteria for treatments are listed in Tables 3, 4, 5 and/or 6. In another aspect, a bacterial composition that is modified to correct a TBI flora to a normal flora is provided before, during, or after undergoing a colon cleanse treatment, delivered by colonoscope, wherein the bacterial composition is not a fecal transplant, or wherein bacteria are lab-grown, or wherein bacteria are lab-grown and customized to specifically modify a TBI flora of a specific patient, or one or more bacteria listed in Tables 3, 4, 5, or 6 as being different from a patient with a brain injury when compared to a normal patient.

BRIEF DESCRIPTION OF THE DRAWINGS

For a more complete understanding of the features and advantages of the present invention, reference is now made to the detailed description of the invention along with the accompanying figures and in which:

FIG. 3A shows differences in the relative abundance of the indicated phyla. FIG. 3B illustrates outcomes for selected families. Significant differences are indicated by asterisks and detailed in the results section.

FIGS. 4B and 4C show the average abundance and standard error for each selected target as indicated in the results section. No differences were observed in 16S abundance or human genomic DNA content. Significant differences are indicated by the asterisks. Detailed data are provided in Table 2.

DETAILED DESCRIPTION OF THE INVENTION

Figure 1A:
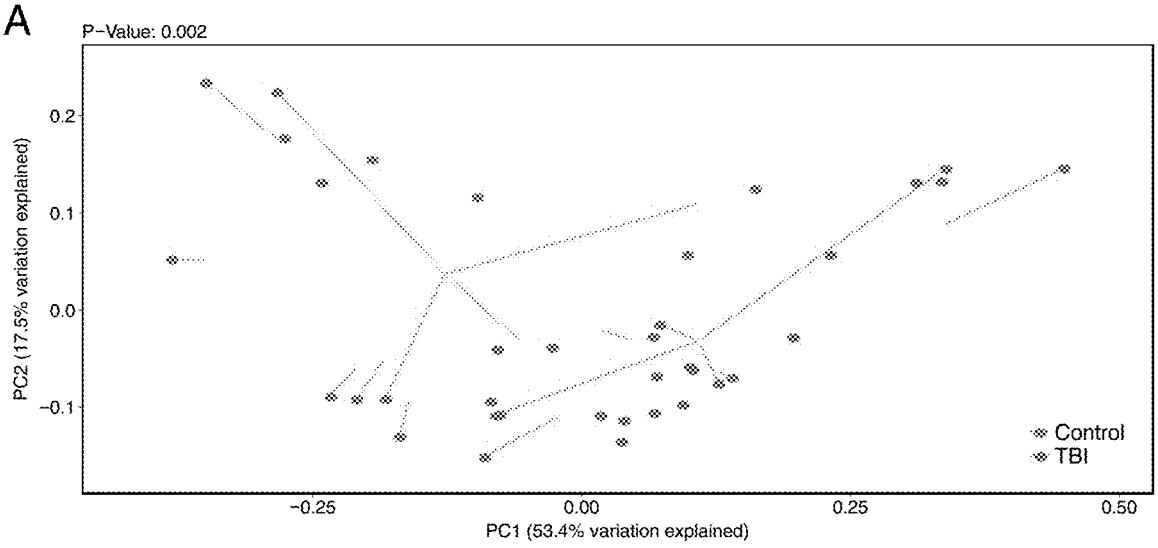
FIGS. 1A and 1B show a comparison of fecal microbiome community structure of TBI and control cohorts determined by 16S V4 NGS. Weighted (FIG. 1A) and unweighted (FIG. 1B) UniFrac principal component analyses (PCoA) were completed to determine if the microbiome community profiles were different between the cohorts. Weighted analysis showed significant differences when considering relative abundance (p=0.002). Unweighted comparisons for the presence or absence of bacterial OTUs also established significantly different profile (p=0.005).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention provides, for the first time, a direct link between altered cognition/fatigue experienced by patients with a traumatic brain injury (TBI) and the gastrointestinal microbiome. This altered cognition or syndrome is referred to as Brain Injury Associated Fatigue and Altered Cognition (BIAFAC), as it was found to include shifted bacterial communities in fecal materials. It was found that patients, who had suffered a TBI when compared to a control group, had a significantly altered microbiome that was associated with the reduced cognition.

The present inventors identified that the microbiome of patients with BIAFAC lacks *Prevotella* spp and *Bacteroidies* spp. Conversely, bacteria in the *Ruminococcaceae* genus are increased in abundance compared to healthy control samples. This work identified specific organisms by both next generation sequencing and quantitative PCR approaches that form the basis of both diagnostic and therapeutic inventions described herein. The inventors identified novel, therapeutically relevant biomarkers that can be used to treat symptomatic, chronic TBI patients, and offering clinically meaningful treatment options for TBI-related comorbidities. Given the complexity of the impact on both the brain, CNS, immune, metabolic, inflammatory, pituitary, and intestinal microbiome, the results herein yielded both therapeutic and mechanistic insights into TBI. The result herein show that supplementation or replacement of the dysbiotic intestinal community via, e.g., fecal microbiota transplant (FMT) can be used to treat TBI patients and its associated comorbidities.

For enhanced diagnostics, the present invention used a qPCR array to diagnose individuals with BIAFAC-associated gastrointestinal (GI) microbiome changes and to monitor the success of therapeutic approaches. Another such array uses customized qPCR assays assembled into kitted systems for use in clinical microbiology facilities. The array can be used to identify optimal donated fecal material from healthy donors to support development of therapeutic microbiome transplants. The therapeutic composition that include oral compositions, suppositories and/or enemas that include supplementation with identified and cultured probiotic organisms reduced or lost in the GI microbiome of BIAFAC patients.

The probiotic bacteria, prebiotic agents, and/or xenobiotics for use with the present invention can be provided in a variety of dosage forms. For example, e.g., tablets, capsules, pills, powders, granules, elixirs, tinctures, suspensions, syrups, enemas, suppositories, and emulsions may be used to provide the probiotic bacteria, prebiotic agents, and/or xenobiotics of the present invention to a patient in need of therapy for brain injury associated fatigue and/or altered cognition.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

For example, the probiotic bacteria, prebiotic agents, and/or xenobiotics may be included in a tablet. Tablets may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with a non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

In one embodiment, gelatin capsules (gelcaps) may include the probiotic bacteria, prebiotic agents, and/or xenobiotics, and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the probiotic bacteria, prebiotic agents, and/or xenobiotics may be adapted for oral administration. Examples of suitable liquid dosage forms include powders, tablets, gelcaps, solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, emulsifying agents, suspending agents, diluents, sweeteners, thickeners, and melting agents, mixtures thereof, and the like, that do not affect the viability of the probiotic bacteria or enhance the viability of the probiotic bacteria.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water soluble salt of the active ingredient, suitable stabilizing agents, and if necessary, buffering salts. Antioxidizing agents such as sodium bisulfite, sodium sulfite and/or ascorbic acid, either alone or in combination, are suitable stabilizing agents. Citric acid and its salts and sodium EDTA may also be included to increase stability. Suitable pharmaceutical carriers are described in REMINGTON'S PHARMACEUTICAL SCIENCES, Mack Publishing Company, a standard reference text in this field, relevant portions incorporated herein by reference.

Patients with chronic traumatic brain injury (TBI) requiring long-term, permanent care suffer a myriad of clinical symptoms (e.g., impaired cognition, fatigue, and other conditions) that persist for many years beyond the acute brain injury. In addition to these comorbid clinical symptoms, chronic TBI patients also exhibit altered amino acid and hormonal profiles with distinct cytokine patterns suggestive of chronic inflammation. The present inventors recognized that this metabolic link could involve a role for the gut-brain axis in chronic TBI. Thus, the inventors utilized a two-site trial to investigate the role of the gut-brain axis in the comorbidities of chronic TBI. The fecal microbiome profile of 22 moderate/severe TBI patients residing in permanent care facilities in Texas and California was compared to 18 healthy age-matched control subjects working within the participating facilities. Each fecal microbiome was characterized by 16S(V4) rRNA gene sequencing and metagenomic genome sequencing approaches followed by confirmatory full 16S rRNA gene sequencing or focused tuf gene speciation and specific qPCR evaluation of selected genera or species. The average chronic TBI patient fecal microbiome structure was significantly different compared to the control cohort, and these differences persisted after group stratification analysis to identify any unexpected confounders. Notably, the fecal microbiome of the chronic TBI cohort had absent or reduced *Prevotella* spp and *Bacteroidies* spp. Conversely, bacteria in the *Ruminococcaceae* family were higher in abundance in TBI compared to control profiles. Although the sequelae of gut-brain axis disruption following TBI is not fully understood, characterizing TBI-related alterations in the fecal microbiome provides biomarkers and therapeutic targets to address patient morbidity.

Traumatic brain injury (TBI) and its accompanying chronic morbidities affects more than 2.5 million individuals annually in the United States[1]. Concern about the long-term effects of brain injury has grown recently with increased publicity of sport-related chronic traumatic encephalopathy[2] and military blast-related injury[3]. TBI is a complex neurologic insult that can lead to chronic, progressive deterioration of patient health and increased morbidity. During convalescence, TBI-associated pathologies can advance to full disability after significant periods of relative health and normalcy. In the case of chronic TBI, where the severity of the injury often requires residence in a long-term care facility, the clinical symptoms are often complex and varied ranging from cognitive deficiencies to fatigue. In this patient population, supportive treatment is standard of care and additional understanding is needed to open new therapeutic avenues.

The sequelae of chronic TBI are not well understood. Aside from the recognized pituitary dysfunction that occurs in some patients, the cause(s) of the myriad of other long-term clinical symptoms and their mediators are uncertain. In the inventors' prior work, chronic TBI patients were found to exhibit abnormal metabolic responses and altered relationships between circulating amino acids, cytokines, and hormones[2]. The present inventors that the gut-brain axis may be linked to neuropathologies[4-7].

Notably, the inventors recognized the interactions between the gastrointestinal (GI) tract, immune system and brain has led to a number of discoveries suggesting that the GI microbiome is a major influence on each of the systems". Further, recent next generation sequencing (NGS) analyses have associated altered GI microbiomes with a growing list of neuropathologies including Parkinson's disease, autism, Guillain-Barre syndrome, anxiety and depression". The GI microbiome is one of the most diverse communities of bacteria in the human body with estimates of up to 1,000 distinct species included in typical communities[12,13]. Current understanding is largely based on fecal analyses by NGS of the variable regions of the bacterial 16S rRNA gene or metagenomic analyses[13]. The large datasets created from various cohorts have clearly established that this community of bacteria contributes to basic physiology, immunity and inflammation. More recently, dysbiosis has been associated with altered cognition, behavior and even mood disorders[4-6].

Mild TBI is associated with alterations in gut metabolism soon after injury with direct impacts upon the intestinal mucosa including loss of tight junctions that contribute to increased intestinal permeability, inflammation and malabsorption[14,15]. Patients with mild TBI can also develop sequelae years after injury presenting with profound fatigue and altered cognition. By way of explanation, and not a limitation of the present invention, the inventors recognized that mucosal alterations likely foster dysbiotic conditions to which the intestinal microbiota adapt ultimately establishing an altered bacterial population that propagates the sequelae.

The present inventors determined whether the fecal microbiome is altered in chronic, moderate-severe TBI patients in permanent care facilities compared to healthy control subjects working at the facilities. The inventors further determined if TBI-induced dysbiosis indeed disrupts the gut/brain axis. It was found that the fecal microbiome provides both biomarkers and therapeutic targets to address additional sequelae observed in chronic TBI patients.

Ethics statement. All patients provided informed consent before blood drawing or collection of a fecal sample was attempted. All procedures were approved by the associated IRBs contracted by the Tideway facility at the Transitional Learning Center (TLC Galveston, Tex.) and Centre for Neuro Skills (CNS; Bakersfield, Calif.). Samples were assigned a unique study number to minimize exposure of personal information.

Patients. Study participants were enrolled from the Tideway TLC facility in Galveston, Tex. or the CNS facility in Bakersfield, Calif. Twenty-two participants with moderate to severe TBI were recruited to provide fecal samples. Eighteen individuals were recruited to the control cohort composed primarily of facility workers who shared both environment and some meals with the TBI patients. After informed consent was obtained, participants were fed a standardized meal and blood was collected 90 minutes later for serum amino acid analysis. Participants were provided fecal sampling kits and were instructed on sampling technique. Fecal samples were collected as close to ingestion of the study meal as possible. In some cases, fecal sampling was completed by caregivers on behalf of the TBI participants. The demographics and details of each cohort are provided in Table 1.

Microbiome analysis and DNA preparation. Preparation of DNA. Fecal samples were shipped to the Baylor College of Medicine's Alkek Center for Metagenomics and Microbiome Research facility on dry ice after being frozen and stored at −80° C. in the stabilizing chemical mixture provided in the DNA Genotek OMNIgene GUT kit (Genotek, Ottawa, Canada). Following an initial thaw of the material, cell lysing and DNA extraction were performed using the Qiagen processing protocol (described in detail for Illumina NGS below) recommended by the NIH-Human Microbiome Project[16,17]. At UTMB, a second DNA extraction was performed on the original fecal material (described in detail below for Ion Torrent full 16S rRNA gene NGS or subsequent qPCR analyses). For both approaches, DNA quality was assessed for total bacterial content and human genomic material via qPCR.

16S rRNA gene sequencing and compositional analysis. 16S rRNA gene sequencing methods were adapted from the methods developed by the NIH-Human Microbiome Project[16,17]. Bacterial DNA was extracted using the PowerMag Microbiome DNA isolation kit following the manufacturer's instructions. The V4 region of the 16S rRNA gene was amplified by PCR and sequenced using barcoded Illumina adapter-containing primers 515F and 806R[18] on the MiSeq platform (Illumina) using the 2×250 bp paired-end read protocol yielding pair-end reads that overlap almost completely. Sequencing read pairs were demultiplexed based on the unique molecular barcodes, and reads were merged using USEARCH v7.0.1090[19]. Merging allowed zero mismatches with a minimum overlap of 50 bases, and merged reads were trimmed at the first base with a Q<5. In addition, a quality filter was applied to the resulting merged reads and those containing above 0.05% expected errors were discarded. Sequences were stepwise clustered into operational taxonomic units (OTUs) at a similarity cutoff value of 97% using the UPARSE algorithm[20]. Chimeras were removed using USEARCH v7.0.1090. OTUs were determined by mapping the centroids to the SILVA database[21] containing only the 16S rRNA gene V4 region to determine taxonomies. A custom script constructed a rarefied OTU table (rarefaction was performed at only one sequence depth) from the output files generated in the previous two steps for downstream analyses. The inventors utilized multiple quality control measures, including the use of non-template controls, at the microbial DNA extraction, 16S rRNA gene amplification, and amplicon sequencing processes. Resulting OTU tables were rarified to 5,953 reads per sample.

Metagenomic shotgun sequencing and analysis. Individual libraries constructed from each sample were sequenced using the 2×100 bp paired-end read protocol on the HiSeq platform (Illumina). The process of quality filtering, trimming and demultiplexing was performed using a pipeline developed at the Baylor College of Medicine that employs a number of publicly available tools such as Casava v1.8.3 (Illumina) for the generation of fastqs, Trim Galore and cutadapt[22] for adapter and quality trimming, and PRINSEQ[23] for sample demultiplexing. Additionally, Bowtie 2 v2.2.1[24] was used to map reads to custom databases for bacteria, viruses, human, and vectors and remove non-bacterial reads from the dataset. For bacterial reads, the highest identity match was chosen. If there were multiple top hits, the lowest common ancestor was determined, but these reads did not contribute to the analysis. Reads whose genomic coordinates overlapped with known KEGG orthologs (KOs) were tabulated. Coding sequences from reference genomes that have not been specifically annotated by KEGG were aligned to all known KOs. Any coding sequence that had >70% identity and >70% query coverage to a known KO was assigned to that KO. This process in effect created links between new genomes and the KEGG database. KEGG modules (M numbers) were calculated step-wise and determined to be complete if 65% of the reaction steps were present per detected species and for the metagenome as a whole. Pathways were constructed for each taxa and metagenome by calculating the minimum set through MinPath[25] resulting from the gene orthologs present. The number of reads matching a KEGG module was averaged across the TBI or control cohorts and compared (unpaired Student's T test) to identify modules that were significantly over or under represented by the TBI microbiome profiles.

Ion torrent 16S rRNA gene NGS and qPCR evaluations. To confirm the 16S rRNA gene NGS, the second preparation of DNA was analyzed by Ion Torrent 16S NGS and qPCR at UTMB for selected organisms. This second DNA preparation addressed differences in recovered DNA species created by different kits as well as the age of the previously extracted material. For the second extraction, after thawing the original material preserved in the OmniGene kit solution, suspended fecal matter was diluted 1:1 in RNeasy PowerMicrobiome kit-provided lysis solution was incubated at 55° C. for 30 minutes (Qiagen, Germantown, Md.) and then subjected to bead beating utilizing 0.1 mm glass bead-based (Qiagen) homogenization (5 minutes at 30 Hz) in a TissueLyser LT (Qiagen). Clarified liquid fractions (13,000×g for 1 minute) were mixed with IRS solution (Qiagen) and incubated at 4° C. for 5 minutes prior to final extraction of DNA using a MagNA Pure 96 automated nucleic acid extraction DNA and viral NA small volume kit (Roche Applied Science, Indianapolis, Ind.).

Ion Torrent fecal microbiome sequencing was carried out using a fusion-PCR method. Briefly, fusion-primers were designed in accordance with the manufacturer's guidelines (Ion Amplification Library Preparation—Fusion Method, Life Technologies, Carlsbad, Calif.) using Ion Xpress Barcodes linked to 16S gene primer pairs targeting 5 overlapping contigs that covered hyper-variable regions 1-8 sequencing over 90% of the gene[26]. DNA from 36 individual fecal samples were stratified into 10 bio-pools created by equal mixing of individual material that then were used as templates for creation of fusion 16S libraries. Stratification was accomplished for healthy control samples based solely upon BMI (above or below 30) creating 2 bio-pools (Table 1). TBI samples were stratified by location, BMI, and whether residence time was above or below the median time participants lived in either the Bakersfield (average of 232 months) or Tideway (average of 241 months) facility creating an additional 8 bio-pools (Table 1). Fusion PCR libraries, generated in a c1000 thermocycler (Bio-Rad), were purified using QIAquick spin-columns (Qiagen) and quantified using a spectrophotometer (Bio-Rad) before being diluted and then sequenced on an Ion Torrent Personal Genome Machine using 400 base pair read kits together with 316 size chips following the manufacturer's instructions (Life Technologies). One TBI bio-pool (BP #3) failed to meet minimal quality metrics and was not analyzed further. Sequencing reads from the other 9 libraries were filtered for quality and binned according to Ion Xpress barcodes using Ion Torrent Suite software (v5.0.5). Filtered sequencing reads in FASTQ format were normalized using the FASTQ groomer tool function in the web-based Galaxy software[27]. Next, each barcoded read was trimmed to remove primer sequences and filtered to the expected size before being compared to the SILVA 16S rRNA gene database using Bowtie 2 software[24,28] Curated reads showed >98% alignment to the database and ranged from 8E5 to 1.2E6 sequences to establish genera level hit-rates. Where multiple calls to the same genera were made the number of hits were added accordingly. These numbers were then converted to percentage of total to give an overall relative proportion for each bio-pool.

Average values for each subgroup are shown in bold text with (SDEV) indicated. Biopool (BP) assignments for the second round of Ion Torrent-based NGS testing are indicated. Several fecal DNA samples were of insufficient quality for molecular evaluations and were not tested (NT) in the biopools but were recovered for subsequent qPCR assays. *Bakersfield controls were significantly younger (p<0.05) than any other subgroup but the overall average age of controls and participants with TBI was not significantly different. There were no differences in average height or weight among the subgroups or main cohorts, however, the controls from Bakersfield had a significantly higher average BMI than the Galvestonians with TBI (p=0.0087) and the combined TBI cohort (p=0.03).

Ion Torrent Sequencing of the tuf gene for *Bacteroides* and *Prevotella* genera also was performed through fusion-primer design using Ion Express barcodes. Two sets of

TABLE 1

Study Cohort Demographics

| ID | Group | Study # | Location | Gender | Age | Height (cm) | Weight (kg) | BMI | Ambulatory | Time since injury (mos) | BP # |
|---|---|---|---|---|---|---|---|---|---|---|---|
| 1 | TBI | 1A | Galveston | M | 34 | 182.9 | 80.6 | 24.1 | N | 27 | 8 |
| 2 | TBI | 2A | Galveston | M | 42 | 193.0 | 82.8 | 22.2 | N | 264 | 10 |
| 3 | TBI | 3A | Galveston | M | 51 | 182.9 | 97.2 | 29.1 | N | 520 | 7 |
| 4 | TBI | 4A | Galveston | M | 52 | 193.0 | 86.9 | 23.3 | N | 177 | 9 |
| 5 | TBI | 6A | Galveston | M | 54 | 181.6 | 70.2 | 21.3 | N | 400 | 10 |
| 6 | TBI | 9A | Galveston | M | 54 | 188.0 | 95.0 | 26.9 | N | 423 | 7 |
| 7 | TBI | 10A | Galveston | F | 60 | 167.6 | 90.5 | 32.2 | N | 218 | 8 |
| 8 | TBI | 7A | Galveston | M | 63 | 185.4 | 68.4 | 19.9 | Y | 173 | NT |
| 9 | TBI | 8A | Galveston | M | 71 | 182.9 | 72.0 | 21.5 | Y | 146 | 9 |
| | Average (SD) | | | 8M/1F | 53.4 (10.9) | 184.1 (7.6) | 82.6 (10.7) | 24.5 (4.1) | 6N/2Y | 260.9 (157) | |
| 10 | TBI | B11 | Bakersfield | M | 50 | 180.34 | 101.8 | 31.3 | N | 315 | 3 |
| 11 | TBI | B12 | Bakersfield | M | 54 | 187.96 | 98.6 | 27.9 | N | 326 | 3 |
| 12 | TBI | B13 | Bakersfield | M | 36 | 176.53 | 87.3 | 28.0 | Y | 252 | 3 |
| 13 | TBI | B14 | Bakersfield | M | 57 | 170.18 | 77.3 | 26.7 | Y | 205 | 5 |
| 14 | TBI | B15 | Bakersfield | M | 47 | 180.34 | 57.7 | 17.7 | N | 264 | 6 |
| 15 | TBI | B16 | Bakersfield | M | 39 | 167.64 | 76.8 | 27.3 | Y | 242 | 6 |
| 16 | TBI | B17 | Bakersfield | M | 62 | 172.72 | 70.9 | 23.8 | Y | 97 | 5 |
| 17 | TBI | B18 | Bakersfield | M | 51 | 193.04 | 105.9 | 28.4 | Y | 206 | 4 |
| 18 | TBI | B19 | Bakersfield | M | 28 | 180.34 | 102.3 | 31.4 | N | 98 | 4 |
| 19 | TBI | B20 | Bakersfield | M | 39 | 167.64 | 72.3 | 25.7 | Y | 192 | 5 |
| 20 | TBI | B21 | Bakersfield | M | 36 | 179.07 | 106.8 | 33.3 | Y | 232 | 3 |
| 21 | TBI | B22 | Bakersfield | M | 67 | 165.1 | 83.2 | 30.5 | Y | 456 | 3 |
| 22 | TBI | B23 | Bakersfield | M | 60 | 172.72 | 69.1 | 23.2 | Y | 101 | 5 |
| | Average (SD) | | | 13M | 48.2 (11.8) | 176.4 (8.2) | 85.4 (16.2) | 27.3 (4.1) | 8Y/5N | 229.7 (101.5) | |
| 23 | Control | 1B | Galveston | M | 33 | 175.26 | 74.3 | 24.2 | Y | N/A | 2 |
| 24 | Control | 2B | Galveston | M | 40 | 193.04 | 103.5 | 27.8 | Y | N/A | 2 |
| 25 | Control | 3B | Galveston | M | 49 | 175.26 | 119.3 | 38.8 | Y | N/A | 1 |
| 26 | Control | 4B | Galveston | M | 50 | 182.88 | 83.3 | 24.9 | Y | N/A | NT |
| 27 | Control | 5B | Galveston | M | 57 | 177.8 | 83.3 | 26.3 | Y | N/A | 2 |
| 28 | Control | 10B | Galveston | F | 60 | 160.02 | 60.8 | 23.7 | Y | N/A | 2 |
| 29 | Control | 6B | Galveston | M | 61 | 175.26 | 103.5 | 33.7 | Y | N/A | 1 |
| 30 | Control | 7B | Galveston | M | 62 | 175.26 | 74.3 | 24.2 | Y | N/A | 2 |
| 31 | Control | 9B | Galveston | M | 66 | 167.64 | 65.3 | 23.2 | Y | N/A | 2 |
| | Average (SD) | | | 8M/1F | 53.1 (11) | 175.8 (9.2) | 85.3 (19.6) | 27.4 (5.4) | 9Y | N/A | |
| 32 | Control | A14 | Bakersfield | M | 24 | 185.42 | 85.5 | 24.9 | Y | N/A | 2 |
| 33 | Control | A19 | Bakersfield | M | 29 | 182.88 | 86.8 | 26.0 | Y | N/A | NT |
| 34 | Control | A16 | Bakersfield | F | 31 | 162.56 | 95.5 | 36.1 | Y | N/A | 1 |
| 35 | Control | A13 | Bakersfield | M | 32 | 172.72 | 104.5 | 35.0 | Y | N/A | 1 |
| 36 | Control | A12 | Bakersfield | F | 34 | 160.02 | 85.9 | 33.5 | Y | N/A | 1 |
| 37 | Control | A21 | Bakersfield | M | 34 | 167.64 | 104.5 | 37.2 | Y | N/A | 1 |
| 38 | Control | A11 | Bakersfield | F | 39 | 162.56 | 84.1 | 31.8 | Y | N/A | 1 |
| 39 | Control | A20 | Bakersfield | F | 39 | 170.18 | 100.0 | 34.5 | Y | N/A | NT |
| 40 | Control | A15 | Bakersfield | M | 43 | 177.8 | 120.5 | 38.1 | Y | N/A | 1 |
| | Average (SD) | | | 5M/4F | 33.9 (5.8)* | 171.3 (9.2) | 96.4 (12.2) | 33 (4.7)* | 9Y | N/A | |
| | Overall TBI | | | 19M | 50.3 (11.5) | 179.7 (8.8) | 84.3 (14) | 26.2 (4.3) | 8Y/11N | 242.5 (124.6) | |
| | Overall Controls | | | 13M/5F | 43.1 (13.1) | 173.6 (9.2) | 90.8 (16.8) | 30.2 (5.7) | 18Y | N/A | | primers covering conserved areas flanking the hyper-variable regions were designed based on multiple sequence alignment of 13 *Bacteroides* and 14 *Prevotella* species sequences obtained from Genbank. Each primer pair was designed to sequence both DNA strands of the specified gene region (Primer pair 1, F: CAAACCGCATGTWAAY-RTTGGTAC (SEQ ID NO:193), R: CCRTC-CATCTGDGCAGCACC (SEQ ID NO:194); Primer pair 2, F: CGTACTTCTBGCHCGTCAGGT (SEQ ID NO:195), R: ACCTGTAGCHACNGTACCACG (SEQ ID NO:196)) producing coverage of approximately 50% of the tuf gene. Data processing and analysis of sequence reads was performed as described above. To identify specific species, NGS-derived tuf sequences were compared against a customized database of reference sequences of *Bacteroides* and *Prevotella* species sequences obtained from Genbank.

qPCR Evaluation.

Based on the sequence data from both approaches and calculated community profiles, qPCR primers were designed using Oligo Architect (MilliporeSigma; Burlington, Mass.) or obtained from the literature (Table 2) to quantify organisms or genera of interest. These assays were evaluated in silico for specificity to their particular genera/species and determined to be specific through amplification of a single PCR product from a bio-pool of the NGS evaluated control and TBI fecal DNAs. PCR products were subsequently cloned and Sanger sequenced authenticating specificity. These cloned amplimers were then used to create high-resolution melt temperatures that served as a further confirmation of identity following SYBR green-based real time amplification. Each 25 μl qPCR was carried out on each fecal DNA sample using: 12.5 μl iQ SYBR green Supermix™ (Bio-Rad), 1 μl of each forward and reverse (5 μM) primer, 9.5 μl nuclease-free water and 1 μl of DNA template. qPCR was completed in a c1000 thermocycler equipped with a CFX™ reaction module (Model info; Bio-Rad). By this method, all but 2 of the fecal samples (controls A19 and A20 failed to meet minimum quality assessments) were successfully evaluated. Fluorescent signal data was collected at the end of each extension step. Starting quantity values were extrapolated from standard curves of plasmids harboring the PCR targets run in parallel for each target.

TABLE 2

Custom fecal microbiome qPCR array details.

| TBI Array Primer | Forward | SEQ ID NO. | Reverse | SEQ ID NO | Target | Reference PMID |
|---|---|---|---|---|---|---|
| Akkermansia | ATTCTCGGTGTAGCAGTG | 1 | CTCAGGCTCAGTTAATGTC | 2 | 16s | This study |
| Alistipes obesi | GGAAGTATCGTCCGTCTC | 3 | AAGTGGATTTTCTTGTTCG | 4 | stL | This study |
| Alistipes onderdonkii | GGCTAAAAGCGTACTGAA | 5 | GTCGATGAAGTAGCTCTC | 6 | DNA polymerase III delta | This study |
| Alistipes putredinis | AAGAATTTCAAGGGTATCATC | 7 | AGGAGAATCGAGAACAAC | 8 | EemA/RhAT Family Transporter | This study |
| Alistipes shahii | GCTTTCCAAGTATGAGTA | 9 | TATATTCGTCAACGCCAG | 10 | tu | This study |
| Alloiococcus | AAAAGAATTGACGGGGAC | 11 | CAAGAGCTGGTAAGGTTC | 12 | 16s | This study |
| Anaerotruncus colihominis | AACAGAGATTGAAGCGGATG | 13 | GGCGGATCATATCAAGGAA | 14 | DNA polymerase beta | This study |
| Asteroleplasma | TACTTCCGGTCTGGGGTG | 15 | TTCTTCCGCGTATCAGTG | 16 | 16s | This study |
| Bacteroides caccae | GCTCTGGTTACTGAACTGGCA | 17 | CAGATCGACCGACATGGGT | 18 | DNA polymerae III alpha | This study |
| Bacteroides clarus | GTATCGCTGTAGGTATGG | 19 | CCTCAATGTCAATATCGTTAT | 20 | gyrA | This study |
| Bacteroides congonensis | ACCACCTCTTCACCGTAA | 21 | TGTCACTTGCTCTACTTGTAAT | 22 | dnaJ | This study |
| Bacteroides coprocola | CGGAGACTTGTTAGTTCTTATCG | 23 | GGTTGTATATCAGGTCGCTTTC | 24 | dnaJ | This study |
| Bacteroides coprophilus | TGTGGTAACTGCTTATCTG | 25 | CATTCTGTCTTGGTCTTGA | 26 | gyrA | This study |
| Bacteroides dorei | TAATACGATCATCCGCTAT | 27 | GCTTGTAAACCTACTTTGT | 28 | recA | This study |
| Bacteroides eggerthii | TATCGGCGACATTAGTAT | 29 | GTTGTCTTCGTTGATAGTAA | 30 | gyrB | This study |
| Bacteroides faecis | GGTAGTCATTGTCAGAGG | 31 | GTCATCCACTGAATATAATAATTG | 32 | DNA polymerase III epsilon | This study |
| Bacteroides finegoldii | ACGGAAACGTGTATGAC | 33 | TCAGTGAGATGCGTAGTC | 34 | gyrB | This study |
| Bacteroides fragilis | GGCGGTCTTCCGGGTAAA | 35 | CACACTTCTGCGGGTCTTTGT | 36 | gyrB | 20643165 |

TABLE 2-continued

Custom fecal microbiome qPCR array details.

| TBI Array Primer | Forward | SEQ ID NO. | Reverse | SEQ ID NO | Target | Reference PMID |
|---|---|---|---|---|---|---|
| Bacteroides intestinalis | AAGACAATGTGCTTAATGC | 37 | GTAGGTCGTCAGTTTAGTTA | 38 | RNA-directed DNA polymerase | This study |
| Bacteroides massiliensis | AATTGGCTTACCTGAACAAG | 39 | CCGAATGGAACACCTCTT | 40 | gyrB | This study |
| Bacteroides nordii | GGGAGATGCGTCAGATAAC | 41 | GGTCGGTATGTTCAAGTAG | 42 | DNA polymerase | This study |
| Bacteroides ovatus | GGAGGATATTATATTCTGCGTAA | 43 | CCACTGTATGCGTATGAC | 44 | Hypothetical protein (Strain ATCC8483) | This study |
| Bacteroides plebius | ACAAAGGAATCACCATCAC | 45 | TTACGCCTTCTTCTGAGT | 46 | gyrB | This study |
| Bacteroides salyersiae | CCGTTATCTGGAATCATCA | 47 | GATAGCCACTTCGATAGG | 48 | gyrB | This study |
| Bacteroides sartorii | GGCGGCAAGATTTATCAG | 49 | TATCAGCGGTTCCTACTTC | 50 | gyrB | This study |
| Bacteroides stercoris | GGAAGCCAATATAGACAAGT | 51 | GGGAAATAGCCGAAGAAG | 52 | gyrB | This study |
| Bacteroides sterorirosoris | GCAAGGAGATGAATTATATGACT | 53 | CACATTCCGTTCGTTGAT | 54 | DNA polymerase III delta | This study |
| Bacteroides thetaiotaomicron | TACAATTGCCACAGTACGGAACA | 55 | GCTGACGAACATGACCATAGTTA | 56 | a-1-6 mannanase | 23068949 |
| Bacteroides timonensis | TAGCCAATGATAAGAAGATAGAAG | 57 | TCACGATACGCATACCTT | 58 | gyrA | This study |
| Bacteroides uniformis | AGCAAAGAAGCGAACATT | 59 | GGGAAGTAGCGCGAAGAAA | 60 | gyrB | This study |
| Bacteroides vulgatus | TTATGAAGAGGAACCACTC | 61 | GAATAAGGAAACGCTCAGA | 62 | Coproporphyrinogen III oxidase | This study |
| Bacteroides xylanisolvens | GGAGCATATCGTAAGACTA | 63 | TTGAGCCATTGAATAATCG | 64 | xyn 10A | This study |
| Bifidobacterium bifidum | GATGACGATTCCACCGAG | 65 | TACGAGACATAATCCTTGATGC | 66 | gyrB | This study |
| Bifidobacterium longum | CATGAATCTCGACGATCTGAA | 67 | CAGGCTGGATGTTCTTGG | 68 | DNA polymerase III gamma and tau | This study |

TABLE 2-continued

Custom fecal microbiome qPCR array details.

| TBI Array Primer | Forward | SEQ ID NO. | Reverse | SEQ ID NO | Target | Reference PMID |
|---|---|---|---|---|---|---|
| Bilophila wadsworthia | CCCGCCATTTATGTGAAG | 69 | CGAAGTAGCACATTTCCA | 70 | taurine:pyruvate aminotransferase | This study |
| Blautia | CTGTCATATTGAGTGCC | 71 | GTCAGTTACCGTCCAGTA | 72 | 16s | This study |
| Butyrivibrio | GACTGCTTTTGAAACTGT | 73 | CCTCCTAATATCTACGCATT | 74 | 16s | This study |
| Candida albicans | GGACGTTACCGCCCAAGCAAT | 75 | GCATCGATGAAGAACGCAGC | 76 | ITS | 15680216 |
| Candida glabrata | GAGCAGCAGATTAATAGAG | 77 | TGTTTCGTAGTGAGTGATA | 78 | ITS | This study |
| Clostridium leptum | CGTAGAGGTTCTGGTAGA | 79 | GATTTCTTGGTTCGTCATTT | 80 | rpoD | This study |
| Clostridium sybiosum | GGAGCAGGTATATGTGAA | 81 | CGGCGTATTGATATTGACA | 82 | gyrB | This study |
| Collinsella | AGCATGTGGCTTAATTCG | 83 | CCTGTATGGGCTCCTCTC | 84 | 16s | This study |
| Coprococcus comes | TATATGAATCTGGTTACGGTAT | 85 | TGGCTGATCGGATAAGTA | 86 | tryp-tRNA ligase | This study |
| Coprococcus eutactus | AGACAGGTGATATAGTAAGC | 87 | CGATGTGATTCTTCCAATG | 88 | DNA gyrase subunit A | This study |
| Cross-assembly phage (CPQ 56) | CAGAGTACAAACTCCTAAAAAACGTAGAG | 89 | GATGACCAATAAACAGCCATTAGC | 90 | Single stranded DNA-binding protein | 28700235 |
| Cross-assembly phage (CPQ 64) | TGTATAGATGCTGCTGCAACTGTACTC | 91 | CGTTGTTTTCATCTTTATCTTGTCCAT | 92 | DnaG family primase | 28700235 |
| Desulfovibrio | CCGTAGATATCTGAGGAACATCAG | 93 | ACATCTAGCATCCATCGTTTACAGC | 94 | 16s | 20940602 |
| Dialister | CCTAGTGTAGCGGTGAAA | 95 | GTCAGTTTTCGTCCAGAA | 96 | 16s | This study |
| Dorea | GGGWTAACKGGAGGAAG | 97 | GTTTACCCATTGTAGCA | 98 | 16s | This study |
| Ecoli universal | GTGTGATATATCTACCCGCTTCGC | 99 | AGAACGGTTTGTGGTTAATCAGGA | 100 | Beta-D-glucuronidase | 12401234 |
| Enterococcus faecalis | AGGAGAGCAACAAGATATTACA | 101 | CGTTCCGCCTTCATAAGT | 102 | gyrB | This study |
| Enterococcus faecium | CACGGAGTAGGATCTTCT | 103 | CACGACGATATTCTTGATAGT | 104 | gyrB | This study |
| Enterococcus universal | AGAAATTCCAAACGAACTTG | 105 | CAGTGCTCTACCTCCATCATT | 106 | 23s | 15707628 |

TABLE 2-continued

Custom fecal microbiome qPCR array details.

| TBI Array Primer | Forward | SEQ ID NO. | Reverse | SEQ ID NO | Target | Reference PMID |
|---|---|---|---|---|---|---|
| Eubacterium rectale | ACAGCCATCATCAATCTC | 108 | ACTTGTCATCCTCGTATTC | 109 | gyrA | This study |
| Eubacterium siraeum | TGCTTGCTATTGATAACATTGA | 110 | TTCCTTGAATCGCTCCAT | 111 | gyrA | This study |
| Eubacterium siraeum | ATATACAGGAGGCTATGC | 112 | CGTCTATTACAACAATCTTATC | 113 | ABC Transporter (Strain DSM15702) | This study |
| Faecalibacterium prausnitzii | CCCTTCAGTGCCGCAGT | 114 | GTCGGAGGATGTCAAGAC | 115 | 16s | 26839545 |
| Fusobacterium nucleatum | CAACCATTACTTTAACTCTACCATGTTCA | 116 | GTTGACTTTACAGAAGGAGATTATGTAAAAATC | 117 | Anti-termination protein nusG | 22009989 |
| Fusobacterium | TARGCGGAACTACACAAGTG | 118 | CAGTAATCTGTCCAGTAAGC | 119 | 16s | This study |
| Haemophilus universal | GGAGTGGGTTGTACCAGAAGTAGAT | 120 | AGGAGTGATCCAACCGCA | 121 | 16s | 9574673 |
| Holdemania filiformis | AGCGTTATATCGGACTTAC | 122 | TTCAGCGTAGTGACAATG | 123 | DNA polymerase III gamma | This study |
| Lachnoclostridium | CTRGTGTAGCGGTGAAATG | 124 | ACGTCAGTTACWGTTCCAGT | 125 | 16s | This study |
| Lactobacillus fermentum | TGGCCCAATTGATTGATG | 126 | GCATCTGTTTCCAAATGTTG | 127 | 16s | This study |
| Lactobacillus reuteri | CAGACAAATCTTTGATTGTTAG | 128 | GCTTGTTGGTTTGGGCTCTTC | 129 | 16s-23s ITS | 10856652 |
| Lactobacillus rhamnosus | TGCTTGCATCTTGATTAATTTTG | 130 | GGTTCTTGGATYTATGCGGTATTAG | 131 | 16s | 15243071 |
| Lactobacillus salivarius | ATGGAATTTGGAGATTATGTTT | 133 | TGCTGGGTAATGTGCTTT | 133 | DNA polymerase III alpha | This study |
| Lactobacillus universal | CTCAAAACTAAACAAAGTTTC | 134 | CTTGTACACACCGCCCGTCA | 135 | 16s | 12351242 |
| Lactococcus lactis | GCTAATAACATCAACACTCA | 136 | TAACTGCTGTCAATCTT | 137 | gyrB | This study |
| Leptotrichia | GGAAAKGTGGGTGGAACTA | 138 | GTTATCTTCATCATCGGCATTC | 139 | 16s | This study |
| Megasphaera massiliensis | AAGAATCGTATCGTCGTTACA | 140 | ACAAGTCGGCAATGGATT | 141 | gyrA | This study |

TABLE 2-continued

Custom fecal microbiome qPCR array details.

| TBI Array Primer | Forward | SEQ ID NO. | Reverse | SEQ ID NO | Target | Reference PMID |
|---|---|---|---|---|---|---|
| Methanobrevibacter smithii | GAAAGCGGAGGTCCTGAA | 142 | ACTGAAAAACCTCCGCAAAC | 143 | nif | 21070516 |
| Ordoribacter | GGCGGAATAAGTTAAGTAGC | 144 | CAGGCGTCAGTTAYRGTCT | 145 | 16s | This study |
| Parabacteroides distasonis | CGGTGACTTATTGATCCTTA | 146 | AATAGCAGGTTGTATAACAGA | 147 | dnaJ | This study |
| Parabacteroides goldsteinii | TCTACCTGTCCGACTTGT | 148 | ATCACCGATAACACCTTCA | 149 | dnaJ | This study |
| Parabacteroides merdae | CAACAATGTGCCGAACCT | 150 | CGCTTACCTGCTTCTTCA | 151 | atL | This study |
| Parasutterella excrementihominis | ATGGCTGACGAAGTAGAT | 152 | GGCGATAACCTTTCTTGAT | 153 | dnaJ | This study |
| Prevotella copri | AGATAGGCAATGTGGAGTAT | 154 | ATCTATCGCATCGCTCTC | 155 | DNA polymerase III alpha | This study |
| Prevotella corporis | GAATGAGCCGCACTATAC | 156 | GAATGAGTTGATAACACTTGAA | 157 | rpoB | This study |
| Prevotella disiens | CCAAAGCAGCACAAATGA | 158 | CCACCTTATCAAGTTCAGATG | 159 | polD | This study |
| Prevotella melaninogenica | TATCCGTGAGCGTATGAA | 160 | TTCGTTCCAAAGAATGAGTTA | 161 | rpoB | This study |
| Prevotella stercorea | CAACTATCTTGAGGAGAACC | 162 | CCTTACGTGCTGCGATAC | 163 | gyrB | This study |
| Prevotella spp | GGGATGCGTCTGATTAGCTTGTT | 164 | CTGCACGCTACTTGGCTGGTTC | 165 | 16s | 20305015 |
| Pseudoflavonifractor capillosus | GACGCCATCATCCTCATC | 166 | GACAACCTGCTCCAGAAC | 167 | hsp60 | This study |
| Ruminococcus bicirculans | GAACCGATTGGGACTTCTTA | 168 | GAGGTATCTTCTCCAAGTC | 169 | DNA polymerase III alpha | This study |
| Ruminococcus bromii | GAAGAGCCGAAAATCATC | 170 | GGTCATCAATACGCAAAT | 171 | DNA polymerase III alpha | This study |
| Ruminococcus callidus | AAGAAGAAGATGCCGATCA | 172 | AAGTGCTGGTGTGGTAT | 173 | dnaJ | This study |
| Ruminococcus obeum | TAGCCAAGAAGTATCATCCA | 174 | CACTGTATGCCTCTGTTG | 175 | dnaJ | This study |

TABLE 2-continued

Custom fecal microbiome qPCR array details.

| TBI Array Primer | Forward | SEQ ID NO. | Reverse | SEQ ID NO | Target | Reference PMID |
|---|---|---|---|---|---|---|
| Ruminococcus torques | TTTCTGCCTGATGATACG | 176 | TATTGATATGCTCGGTCTG | 177 | gyrB | This study |
| Streptococcus salivarius | AATCAACAAGAGAACTTTACG | 178 | CATCAACATCTGCTGGTA | 179 | ketol-acid reductoisomerase | This study |
| Streptococcus universal | AGTCGGTGAGGTAACCGTAAG | 180 | AGGAGGTGATCCAACCGCA | 181 | 16s | 9574673 |
| Subdoligranulum | AACCCATAAATTGCTTTCA | 182 | ATATCTACGCATTCCACC | 183 | 16s | This study |
| Sulfate-reducing Bacteria-DSCR1 | ACSCACTGGAAGCACG | 184 | GGTGGAGCCGTGCATGTT | 185 | dsrA | 17351812 |
| Sutterella | CGCGAAAAACCTTACCTAGCC | 186 | GACGTGTGAGGCCCTAGCC | 187 | 16s | 22233678 |
| Veillonella | GACGAAAGTCTGACGGAG | 188 | CCGATTAACAGAGCTTTACAA | 189 | 16s | This study |
| 16s | TCCTACGGGAGGCAGCAGT | 190 | GGACTACCAGGGTATCTAATCCTGTT | 191 | 16s | 14532224 |
| hGAPDH | CAACTACATGGTTTACATGTTC | 192 | CTCGCTCCTGGAAGATG | 193 | hGAPDH | 15927278 |

Amino acid analysis. Postprandial plasma amino acid levels were assessed for both TBI and control subjects as previously described. In summary, following overnight fasting and consumption of a standardized mixed-macronutrient meal, 5 ml of blood was drawn via venipuncture from subjects approximately 90 minutes after completing the meal. Fresh blood was separated by centrifugation at 3,000 RPM for 20 minutes and serum fractions were stored at −80° C. (or on dry ice while in transit from Bakersfield to Galveston) until analysis. Serum amino acid concentrations were determined after protein precipitation using a Hitachi L8800 amino acid analyzer (Hitachi, Tokyo, Japan) according to manufacturer guidelines.

Statistical analysis. Bacterial diversity was assessed by calculating the number of observed OTUs and the Shannon diversity index (SDI) based on 16S rRNA gene compositional analysis. The number of observed OTUs measures bacterial richness in a sample, while SDI measures both richness and evenness. Between sample diversity, or resemblance, was assessed with weighted and unweighted UniFrac metrics and plotted using principal coordinate analysis (PCoA) ordination[29]. To examine the contribution of different taxa to diversity and community composition, the relative abundances of taxa at the OTU, genus, and phylum level were calculated. Diversity data were analyzed using R[30]. Differences between alpha diversity in TBI v. controls were assessed with Wilcoxon rank-sum tests. Differences in beta diversity (Unifrac distance) were assessed using PERMANOVA. All P-values were adjusted for multiple comparisons with the FDR algorithm[31]. MixOmics[32] was implemented in R version 3.3[30] to determine the correlations between the bacterial relative abundance and the concentration of selected amino acids[33]. MixOmics used sparse partial least squares regression (sPLS) and was performed in canonical mode with LASSO penalization. Statistical analyses of the qPCR data were performed using Excel™ (Microsoft Corp., Redmond, Wash.) or Prism (GraphPad, Inc. v7.0e) software packages. Clustering analysis was completed using Morpheus web-based software (Broad Institute, Cambridge, Mass.). For comparisons of the qPCR absolute abundance data, statistical significance was determined using Multiple t tests via the Holm-Sidak method (Prism). Each qPCR target was analyzed individually, without assumption of a consistent SD. A p value of <0.05 was considered significant.

Study Cohort. Fecal samples were collected from a cohort of patients with chronic, moderate to severe TBI residing in permanent care facilities located in Galveston, Tex. and Bakersfield, Calif. (n=22) and from healthy control subjects (n=18). The control cohort was enrolled from the care facilities in an effort to limit potential confounding factors, as they shared both environment and ate some of the same meals with the TBI patients. The demographics of the cohorts are summarized in Table 1. In general, patients from the Texas cohort were minimally medicated while a more aggressive drug therapy approach was utilized in the California cohort. All but one of the TBI samples was collected from participants who had not taken any recent antibiotic treatments. Similarly, only one of the controls was actively taking amoxicillin at the time of fecal sampling. Most of the other medications were oral dietary supplements (e.g., fish oil) or medications related to mood disorders (e.g., Zoloft).

Individuals in the Galveston program resided in private or semi-private rooms within one building. Meals were planned and supervised by a dietician and plated for the individual. When the individuals went on outings, they were free to eat ad lib. Individuals in the Bakersfield program lived in one- or two-bedroom apartments within a large apartment complex. They followed a meal planning menu supervised by a dietician and went to the grocery store to purchase their own food. Meals were prepared by that individual with help as needed and they were also free to eat ad lib when on outings.

There were no significant differences between the two main cohorts (overall TBI versus overall control) regarding average age, height, weight or BMI (multiple t test p>0.05). Comparisons of the average time since TBI injury revealed no differences between the two sites nor were there differences between a facility cohort and the overall average (p>0.99). Considering each facility subgroup, the Bakersfield controls were significantly younger (p<0.05) than any other subgroup but the overall average age of controls and participants with TBI was not significantly different. There were no differences in average height or weight among the subgroups, however, the control cohort from Bakersfield had a significantly higher average BMI than the Galvestonians with TBI (p=0.0087) and the combined TBI cohort (p=0.03). Because weight/BMI differences may be significant contributors to the intestinal microbiome profile, the inventors completed all analyses of 16S gene sequencing data and qPCR outcomes both by comparing the overall TBI versus overall control, and by comparing site-specific control versus site-specific TBI results. This approach also addressed any potential impact for differences in drug therapy regimens between the facilities.

Figure 1B:
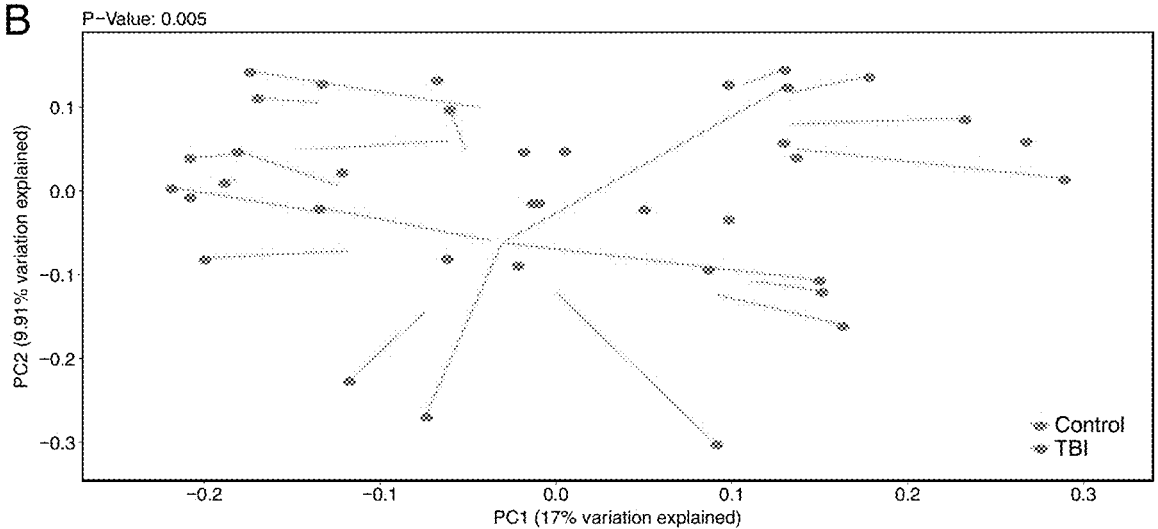

Shifted fecal microbiomes were identified in chronic TBI cohorts compared to controls. Fecal DNA from each person in the cohort was initially evaluated for quality prior to subsequent molecular evaluations. Four samples failed to meet quality metrics for amplifiable DNA (16S gene and human targets) and were excluded from the NGS analyses (Table 1; NT). The remaining DNA samples were subjected to 16S rRNA gene V4 sequencing. Inclusion of all available samples from both collection sites illustrated that the microbiome profiles were significantly different between TBI and controls, both by weighted UniFrac (FIG. 1A; p=0.002) and unweighted UniFrac (FIG. 1B; p=0.005) PCoA analysis. UniFrac is a distance metric that incorporates phylogenetic relatedness of taxa in the analysis. The weighted UniFrac metric considered relative abundance of bacterial OTUs showing that the overall structure of the microbial communities was different between groups (FIG. 1A). The unweighted UniFrac metric evaluated only the presence or absence of bacterial OTUs and demonstrated that the community structure also was significantly different between TBI and controls (FIG. 1B).

Figure 2:
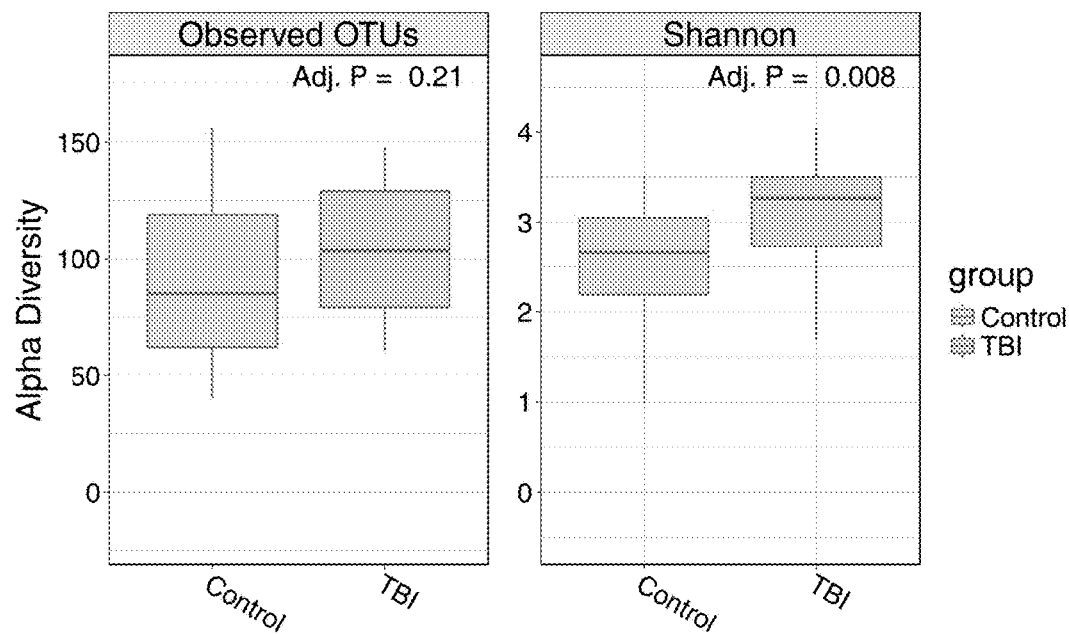
FIG. 2 shows the Alpha and Shannon diversity index (SDI) comparisons between TBI and control cohort community profiles. Overall numbers of OTUs were not statistically different (p=0.21) as shown by alpha diversity calculations were completed using $R^{30}$. The SDI was significantly higher in TBI cohorts compared to controls (p=0.008). Alpha diversity differences between TBI and control datasets were assessed by Wilcoxon rank-sum tests. Evaluation of beta diversity (Unifrac distance) was completed by. PERMANOVA. All P-values were adjusted for multiple comparisons with the FDR algorithm[31].

To evaluate if the observed differences were maintained when only a single location was compared, the inventors reran the weighted UniFrac PCoA analysis between TBI and matched controls from each site, and confirmed that significant differences between TBI and controls persisted in both the Galveston (p=0.002) and Bakersfield (p=0.006) cohorts (not shown). Notably, the overall relative abundance of bacterial genera from samples collected at each site was comparable, and no single genera was found to be significantly different between locations (not shown); supporting a lack of geographical bias and reducing concerns about the impact of other confounders. Next, the inventors compared alpha diversity and bacterial relative abundance between the overall TBI and control groups. The number of observed OTUs was not significantly different between TBI and controls (p=0.21), but the SDI (richness and evenness) was significantly higher in TBI cohorts compared to controls (p=0.008; FIG. 2).

Figure 3A:
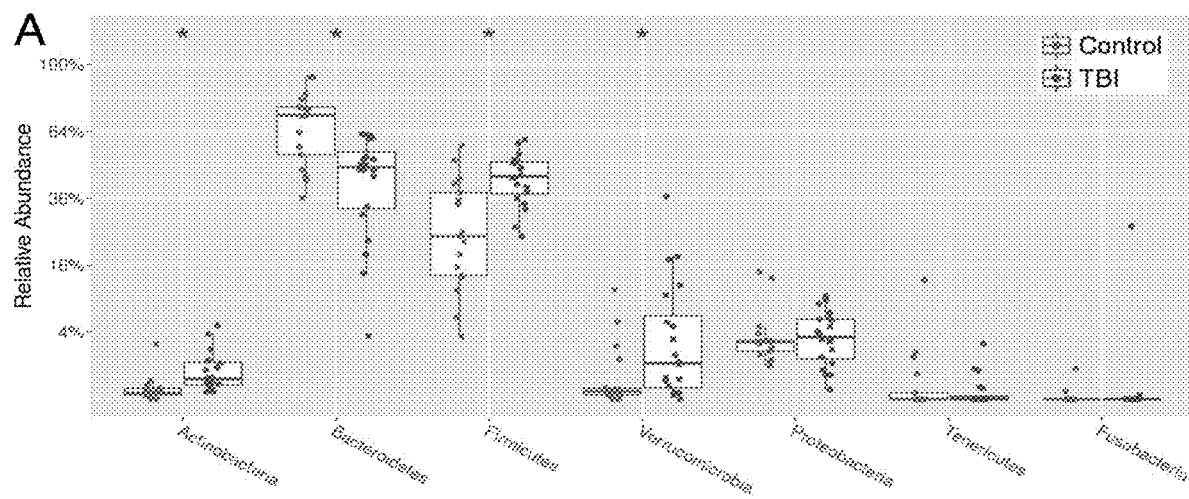
FIGS. 3A and 3B show a comparison of the average relative abundance of indicated OTUs detected in TBI and control fecal bacterial communities. The plots illustrate individual levels for each indicated target (scatter plot) as well as the mean, standard deviations and 95% confidence intervals (box and whiskers).
Figure 3B:
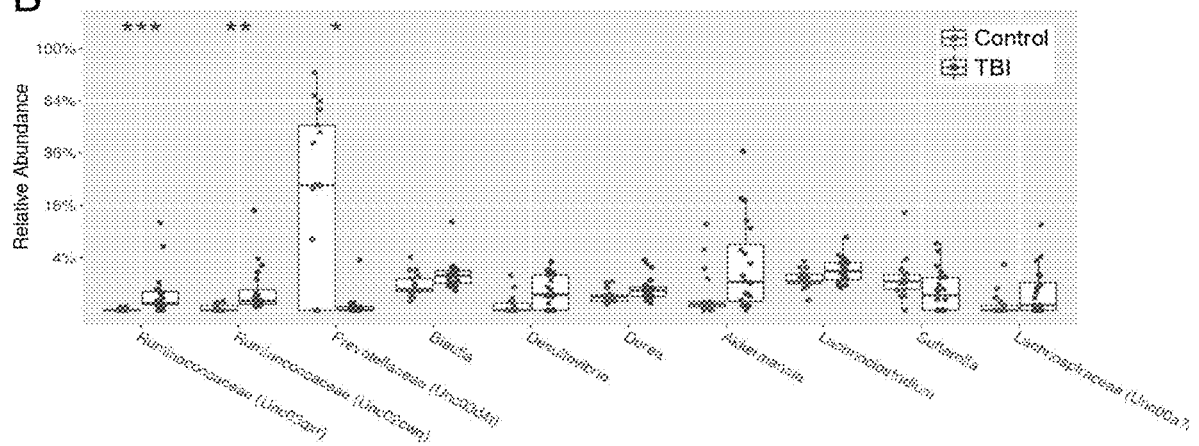

The data revealed that there were significant shifts even at the phyla level when the average TBI community structure was compared to the control cohort. The most abundant bacterial phyla were Bacteroidetes and *Firmicutes*, with the relative abundance of Bacteroidetes significantly higher in controls (p=0.002) and the relative abundance of *Firmicutes* significantly higher in TBI (p=0.002; FIG. 3A). Also, the relative abundance of Actinobacteria (p=0.002) and Verrucomicrobia (p=0.038) were significantly higher in TBI compared to controls (FIG. 3A). At the family level, Prevotellaceae (phylum Bacteroidetes) was significantly more abundant in controls (p=0.03) and, two unclassified genera of *Firmicutes* from the family *Ruminococcaceae* were significantly higher in TBI (p<0.001; FIG. 3B). The relative abundance of the 3 significant bacterial families was indistinguishable between the two collection locations (data not shown).

Because 16S V4 rRNA gene sequencing data are limited to family/genus level analyses, the inventors performed metagenomic shotgun sequencing and analyzed the resulting data at the genus and species levels. These analyses corroborated the 16S rRNA gene evaluations confirming that *Prevotella* was significantly more abundant in controls (p<0.001), and *Ruminiclostridium* trended toward a greater abundance in TBI (p=0.063). Within the metagenomic data, at the species level, *Prevotella stercorea* was significantly higher in controls (p<0.001). However, qPCR assays, described below, targeting two distinct *P. stercorea* genes showed that most samples were negative for this species. Because this organism was found in only a few samples from both controls and TBI, the inventors concluded that other *Prevotella* species were likely missed by the NGS analyses.

To rigorously confirm the differences identified through Illumina 16S V4 and metagenomic comparisons, the inventors also employed a novel NGS approach that utilized Ion Torrent sequencing of five overlapping contigs created by amplification of the bacterial 16S rRNA gene[34]. This method produced bi-directional sequences from >90% of the bacterial 16S rRNA gene including all of the variable regions, but had lower throughput relative to Illumina NGS. As a result, the inventors created 10 bio-pools of fecal DNA (equivalent bacterial genomic contributions of the indicated samples mixed into a single DNA pool), by stratifying the cohorts by BMI, and by time, since TBI (Table 1). Coincidentally, this also led to some Bakersfield- and Galveston-specific bio-pools allowing for more direct comparisons to confirm a lack of collection site effects. One of the libraries (representing bio-pool 3) failed to meet minimal quality criteria and was excluded.

Results from the nine successful bio-pools (two control and seven TBI) corroborated much of the Illumina 16S rRNA V4 and metagenomic data with some exceptions. At the genus level, the control samples had higher average relative abundance of *Prevotella* (88 fold increase over TBI sample average), *Clostridium* (5.7 fold) and *Faecalibacterium* (2 fold; Table 3). Relative to the average control abundance, TBI samples had higher levels of *Akkermansia* (21 fold), *Anaerotruncus* (2 fold), uncultured *Christensenellaceae* (5.7 fold), *Clostridium* (5 fold), *Collinsella* (3 fold), *Desulfovibrio* (4 fold), *Flavonifractor* (4 fold), *Odoribacter* (16 fold), *Parabacteroides* (2.3 fold), *Streptococcus* (8.8 fold; Table 3). Comparisons between bio-pools also indicated no obvious differences associated with collection site or BMI differences.

TABLE 3

Compressed Ion Torrent NGS Results.

| Genus | Control BMI <30 | Control BMI >30 | TBI BP4 | TBI BP5 | TBI BP6 | TBI BP7 | TBI BP8 | TBI BP9 |
|---|---|---|---|---|---|---|---|---|
| *Akkermansia* | 0.05 | | 0.07 | 0.051 | 0.218 | 1.474 | 4.845 | 0.239 |
| *Anaerotruncus* | 0.16 | 0.57 | 0.11 | 0.043 | 1.976 | 1.331 | 0.286 | 0.091 |
| *Alistipes* | 2.41 | 1.99 | 1.92 | 0.593 | 6.010 | 4.053 | 0.299 | 1.142 |
| *Bacteroides* | 25.61 | 17.71 | 32.77 | 25.102 | 1.906 | 15.509 | 14.498 | 9.651 |
| *Blautia* | 4.75 | 1.62 | 1.91 | 7.304 | 2.240 | 4.193 | 1.998 | 3.060 |
| Christensenellaceae uncultured | 0.06 | 0.57 | 1.58 | 0.393 | 2.971 | 0.454 | 0.068 | 2.851 |
| *Clostridium* | 1.48 | 0.18 | 0.05 | 0.142 | 0.181 | 0.368 | | 0.061 |
| *Collinsella* | 0.53 | 1.36 | | 0.263 | 1.689 | 2.144 | 6.686 | 1.175 |
| Coriobacteriaceae uncultured | 0.21 | | | 0.157 | 0.108 | 1.019 | 0.419 | 0.291 |
| *Desulfovibrio* | 0.11 | | 0.52 | | 1.128 | 0.189 | 0.153 | 0.042 |
| *Enterorhabdus* | 0.20 | | | | | | | |
| *Faecalibacterium* | 3.05 | 3.37 | 1.71 | 2.003 | 1.464 | 2.076 | 0.219 | 2.586 |
| *Flavonifractor* | 0.13 | 0.07 | 0.11 | 0.042 | | 0.072 | 1.270 | |
| Lachnospiraceae uncultured | 3.15 | 3.05 | 6.06 | 3.673 | 1.323 | 5.782 | 5.084 | 3.221 |
| *Lactobacillus* | | 2.96 | | 13.568 | 0.036 | | 0.049 | |
| *Odoribacter* | 0.05 | 0.06 | 0.33 | 0.439 | 1.361 | | | |
| *Parabacteroides* | 2.85 | 1.22 | 1.30 | 1.247 | 2.670 | 5.235 | 20.303 | 2.409 |
| *Prevotella* | 8.67 | 17.09 | 0.12 | 0.130 | | | | |
| *Prevotella* uncultured | | | | | | 0.252 | 0.149 | |
| *Roseburia* | 0.42 | 0.61 | 0.04 | 0.469 | | 0.134 | 0.377 | 1.007 |
| Ruminococcaceae uncultured | 2.46 | 6.64 | 4.52 | 2.342 | 12.074 | 8.034 | 5.232 | 10.589 |
| *Ruminococcus* | 7.86 | 10.14 | 2.68 | 18.736 | 4.189 | 11.405 | 0.422 | 1.529 |
| *Streptococcus* | | 0.26 | 4.36 | 3.237 | 0.296 | 3.588 | | |

TABLE 3-continued

Compressed Ion Torrent NGS Results.

| | | | | | | | | |
|---|---|---|---|---|---|---|---|---|
| Subdoligranulum | 1.04 | 1.15 | 0.14 | 0.430 | 0.471 | 2.941 | 0.798 | 1.518 |
| Sutterella | 1.41 | 1.38 | 3.20 | 0.327 | 3.134 | 0.048 | 1.630 | 0.480 |

| Genus | TBI 10 | Control Avg (SDEV) | TBI Avg (SDEV) | Fold-change | Control detects | TBI detects |
|---|---|---|---|---|---|---|
| Akkermansia | 0.649 | 0.05 | 1.08 (1.7) | 20.9 | 1 | 7 |
| Anaerotruncus | 1.365 | 0.37 (0.3) | 0.74 (0.8) | 2.0 | 2 | 7 |
| Alistipes | 1.229 | 2.20 (0.3) | 2.18 (2.1) | −1.0 | 2 | 7 |
| Bacteroides | 1.520 | 21.66 (5.6) | 14.42 (11.53) | −1.5 | 2 | 7 |
| Blautia | 3.801 | 3.18 (2.2) | 3.50 (1.9) | 1.1 | 2 | 7 |
| Christensenellaceae uncultured | 4.313 | 0.32 (0.2) | 1.8 (1.6) | 5.7 | 2 | 7 |
| Clostridium | | 0.83 (0.9) | 0.16 (0.1) | −5.2 | 2 | 5 |
| Collinsella | 5.041 | 0.94 (0.6) | 2.83 (2.5) | 3.0 | 2 | 6 |
| Coriobacteriaceae uncultured | 0.165 | 0.21 | 0.36 (0.3) | 1.7 | 1 | 6 |
| Desulfovibrio | 0.545 | 0.11 | 0.43 (0.4) | 4.1 | 1 | 6 |
| Enterorhabdus | 0.233 | 0.20 | 0.23 | 1.1 | 1 | 1 |
| Faecalibacterium | 1.921 | 3.21 (0.2) | 1.71 (0.7) | −1.9 | 2 | 7 |
| Flavonifractor | | 0.10 (0.04) | 0.37 (0.6) | 3.6 | 2 | 4 |
| Lachnospiraceae uncultured | 2.985 | 3.1 (0.1) | 4.2 (1.8) | 1.3 | 2 | 7 |
| Lactobacillus | | 2.96 | 4.55 (4.6) | 1.5 | 1 | 3 |
| Odoribacter | 1.435 | 0.06).01) | 0.89 (0.6) | 15.8 | 2 | 4 |
| Parabacteroides | 0.295 | 2.04 (1.2) | 4.78 (7) | 2.3 | 2 | 7 |
| Prevotella | 0.187 | 12.88 (6) | 0.15 (0.04) | −87.9 | 2 | 3 |
| Prevotella uncultured | | | 0.20 (0.1) | | 0 | 2 |
| Roseburia | 0.247 | 0.51 (0.1) | 0.38 (0.3) | −1.3 | 2 | 6 |
| Ruminococcaceae uncultured | 9.199 | 4.55 (2.9) | 7.43 (3.5) | 1.6 | 2 | 7 |
| Ruminococcus | 7.684 | 9.00 (1.6) | 6.66 (6.5) | −1.3 | 2 | 7 |
| Streptococcus | 0.174 | 0.26 | 2.33 (2) | 8.8 | 1 | 5 |
| Subdoligranulum | 3.779 | 1.09 (0.1) | 1.44 (1.4) | 1.3 | 2 | 7 |
| Sutterella | 0.262 | 1.39 (0.02) | 1.30 (1.4) | −1.1 | 2 | 7 |

Interrogation of NGS 16S rRNA gene sequences against databases can mask differences in individual organisms that may share closely related sequences. To better differentiate specific organisms in the fecal samples and address the *P. stercorea* outcome noted above, the inventors developed and completed Ion Torrent NGS of the bacterial tuf gene for the *Bacteroides*, *Parabacteroides* and *Prevotella* genera, because of the similarity of their 16S rRNA gene sequences and their differential abundance between control and TBI samples. This approach identified sequence matches to over 70 species within these genera and further confirmed that *Prevotella* spp and *Bacteroides* spp were generally more abundant in healthy controls compared to TBI, with notable exceptions to this generalization (Table 4). The tuf gene results revealed that *P. copri* was the most abundant *Prevotella* species in the controls (73% of tuf gene sequences representing a 54-fold greater abundance than measured in TBI samples) followed by the previously identified *P. stercorea* (4.6% of the control detections and 69-fold more abundant than in TBI samples). *Bacteroides* species that were more abundant in controls included *B. plebius* (3.7% of detections and 19-fold greater abundance) and *B. massilensis* (2.6% and 7-fold). However, this analysis identified specific *Bacteroides* species that were more abundant in TBI samples including *B. uniformis* (32% of detections and 17-fold higher abundance), *B. stercoris* (19.6% of detections and 13-fold higher abundance), *B. dorei* (6.3% of detections and 8-fold more abundant), *B. pectinophilus* (2.4% and 3.6-fold) and *B. vulgatus* (6.5% and 2-fold). Finally, this analysis revealed species that were proportionally rare, but were detected in either controls or TBI samples only (Table 4).

TABLE 4 tuf gene NGS to identify species.

| Genus | Species | Avg Control % | Avg TBI % | TBI Fold-change |
|---|---|---|---|---|
| Prevotella | copri | 73.281 | 1.352 | −54.2 |
| Prevotella | stercorea | 4.575 | 0.066 | −68.9 |
| Bacteroides | plebeius | 3.731 | 0.198 | −18.8 |
| Bacteroides | vulgatus | 3.605 | 6.535 | 1.8 |
| Bacteroides | massiliensis | 2.570 | 0.369 | −7.0 |
| Bacteroides | uniformis | 1.930 | 32.029 | 16.6 |
| Bacteroides | stercoris | 1.518 | 19.607 | 12.9 |
| Bacteroides | caccae | 1.019 | 1.256 | 1.2 |
| Bacteroides | thetaiotaomicron | 0.860 | 1.712 | 2.0 |
| Bacteroides | dorei | 0.799 | 6.335 | 7.9 |
| Bacteroides | pectinophilus | 0.673 | 2.415 | 3.6 |
| Bacteroides | salyersiae | 0.511 | 0.006 | −91.8 |
| Bacteroides | ovatus | 0.476 | 1.660 | 3.5 |
| Bacteroides | xylanisolvens | 0.298 | 1.603 | 5.4 |
| Bacteroides | fragilis | 0.297 | 1.411 | 4.8 |
| Bacteroides | eggerthii | 0.220 | 0.405 | 1.8 |
| Bacteroides | coprocola | 0.207 | 0.006 | −34.9 |
| Parabacteroides | goldsteinii | 0.179 | 0.474 | 2.7 |
| Bacteroides | finegoldii | 0.099 | 0.013 | −7.6 |
| Bacteroides | intestinalis | 0.051 | 0.617 | 12.0 |
| Bacteroides | sartorii | 0.047 | 0.553 | 11.7 |
| Parabacteroides | distasonis | 0.040 | 0.190 | 4.8 |
| Bacteroides | barnesiae | 0.031 | 0.068 | 2.2 |
| Bacteroides | nordii | 0.021 | 0.076 | 3.6 |
| Bacteroides | clarus | 0.018 | 0.034 | 1.9 |
| Bacteroides | congonensis | 0.017 | 0.039 | 2.3 |
| Bacteroides | helcogenes | 0.014 | | |
| Bacteroides | caecimuris | 0.008 | 0.018 | 2.4 |
| Prevotella | buccalis | 0.007 | 0.020 | 2.9 |

TABLE 4-continued tuf gene NGS to identify species.

| Genus | Species | Avg Control % | Avg TBI % | TBI Fold-change |
|---|---|---|---|---|
| Bacteroides | timonensis | 0.007 | 0.003 | −2.6 |
| Bacteroides | stercorirosoris | 0.006 | 0.069 | 11.0 |
| Bacteroides | pyogenes | 0.006 | 0.027 | 4.3 |
| Bacteroides | fluxus | 0.005 | 0.012 | 2.5 |
| Bacteroides | reticulotermitis | 0.003 | 0.003 | −1.1 |
| Prevotella | oris | 0.003 | | |
| Bacteroides | faecis | 0.002 | 0.365 | 156.6 |
| Bacteroides | acidifaciens | 0.002 | 0.007 | 3.0 |
| Prevotella | conceptionensis | 0.002 | | |
| Bacteroides | graminisolvens | 0.002 | | |
| Bacteroides | cellulosilyticus | 0.002 | 0.008 | 5.4 |
| Prevotella | multisaccharivorax | 0.002 | | |
| Bacteroides | salanitronis | 0.001 | 0.006 | 7.4 |
| Prevotella | bryantii | 0.001 | | |
| Prevotella | dentalis | 0.001 | | |
| Bacteroides | ihuae | 0.001 | | |
| Prevotella | jejuni | 0.001 | | |
| Prevotella | maculosa | 0.001 | | |
| Bacteroides | neonati | 0.001 | | |
| Prevotella | bergensis | | 0.0002 | |
| Prevotella | saccharolytica | | 0.0002 | |
| Prevotella | aurantiaca | | 0.0004 | |
| Bacteroides | faecichinchillae | | 0.0004 | |
| Bacteroides | oleiciplenus | | 0.0004 | |
| Prevotella | phocaeensis | | 0.0004 | |
| Bacteroides | luti | | 0.001 | |
| Bacteroides | neonati | | 0.001 | |
| Prevotella | nigrescens | | 0.001 | |
| Bacteroides | paurosaccharolyticus | | 0.001 | |
| Prevotella | oralis | | 0.001 | |

TABLE 4-continued tuf gene NGS to identify species.

| Genus | Species | Avg Control % | Avg TBI % | TBI Fold-change |
|---|---|---|---|---|
| Prevotella | ruminicola | | 0.001 | |
| Bacteroides | gallinarum | | 0.002 | |
| Prevotella | intermedia | | 0.003 | |
| Prevotella | disiens | | 0.005 | |
| Prevotella | ihumii | | 0.009 | |
| Prevotella | brevis | | 0.009 | |
| Bacteroides | helcogenes | | 0.035 | |
| Bacteroides | coprophilus | | 0.079 | |
| Prevotella | corporis | | 0.080 | |

Figure 4A:
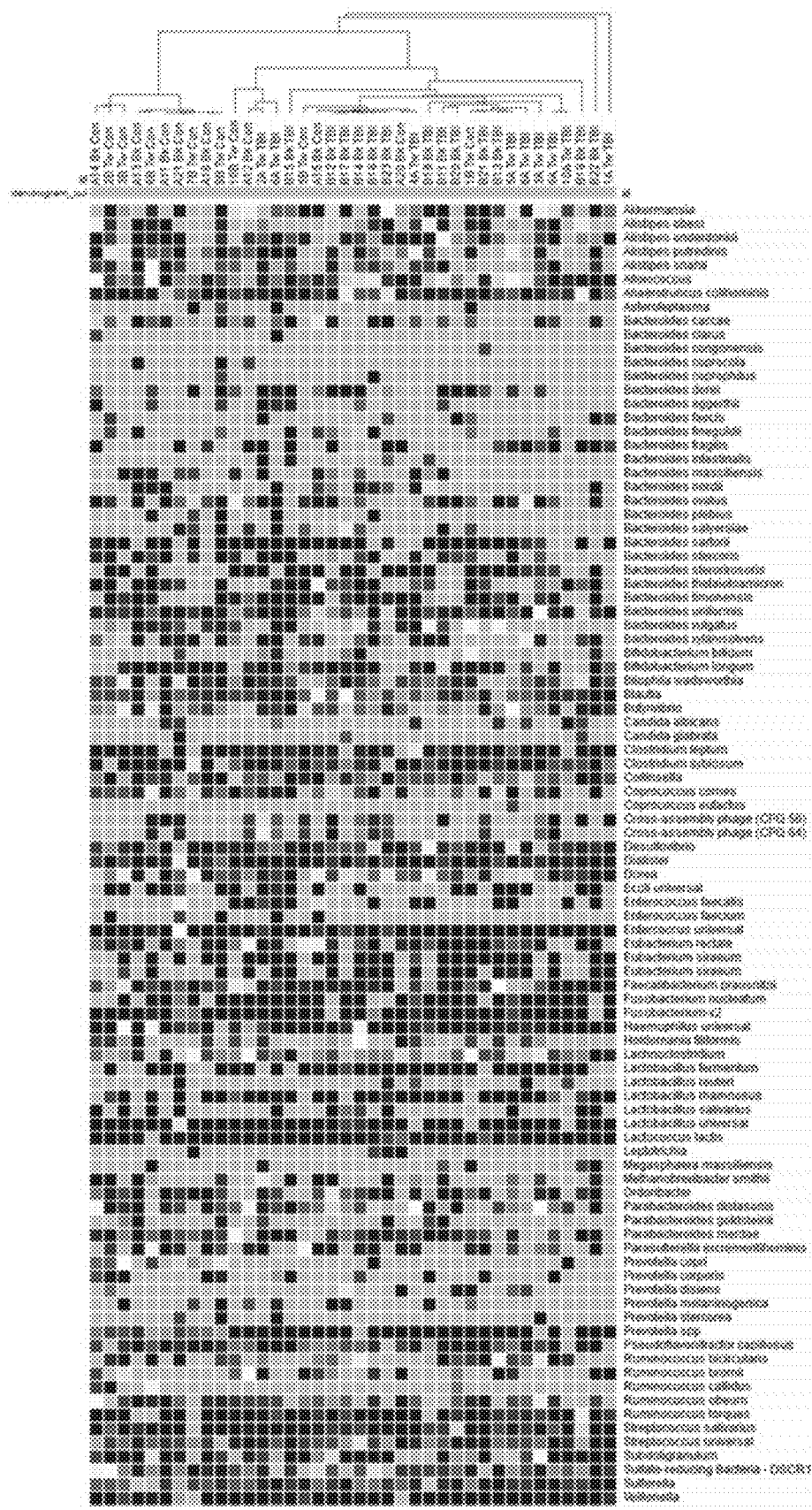
FIGS. 4A to 4C show the significant differences in absolute abundance established by customized fecal microbiome qPCR array. Using a novel 96 target qPCR array developed for this study, absolute abundance for 94 selected bacterial targets and 2 controls (16S rRNA gene and human GAPDH gene) supported clustering analysis using Morpheus web-based software (Broad Institute, Cambridge, Mass.) was completed on individual TBI and control profiles as shown in FIG. 4A. Statistically significant differences in the average qPCR absolute abundance data was determined using multiple t tests via the Holm-Sidak method (GraphPad Prism, v.7.0e).
Figure 4B:
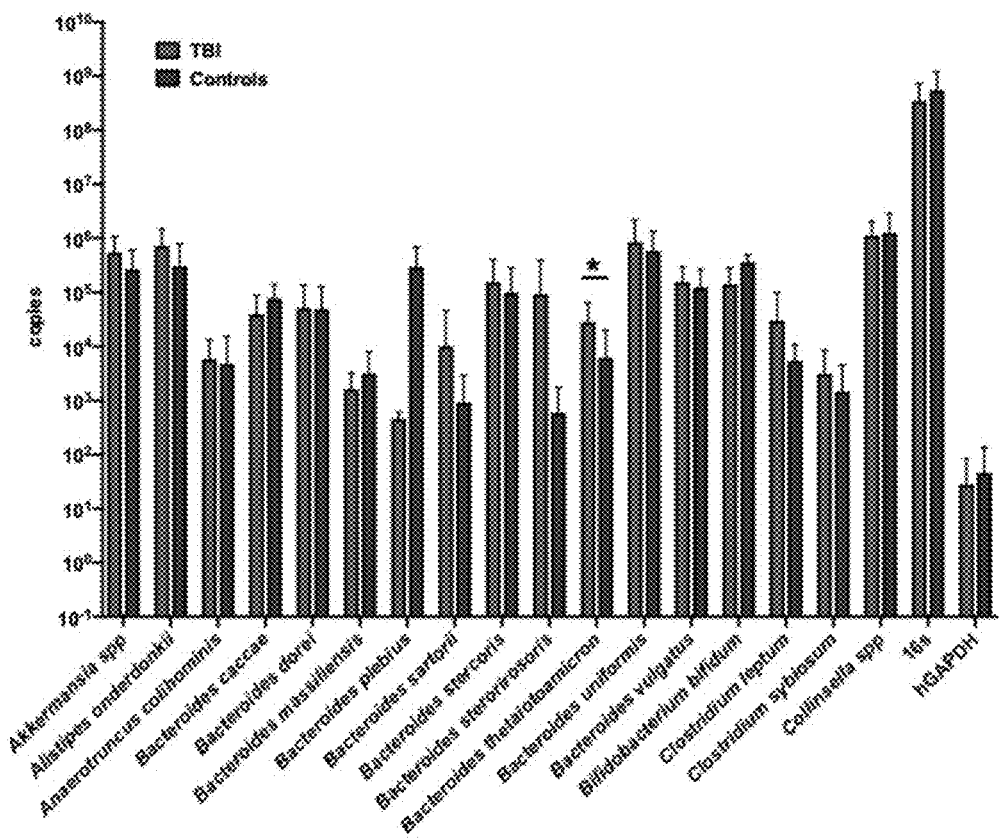
Figure 4C:
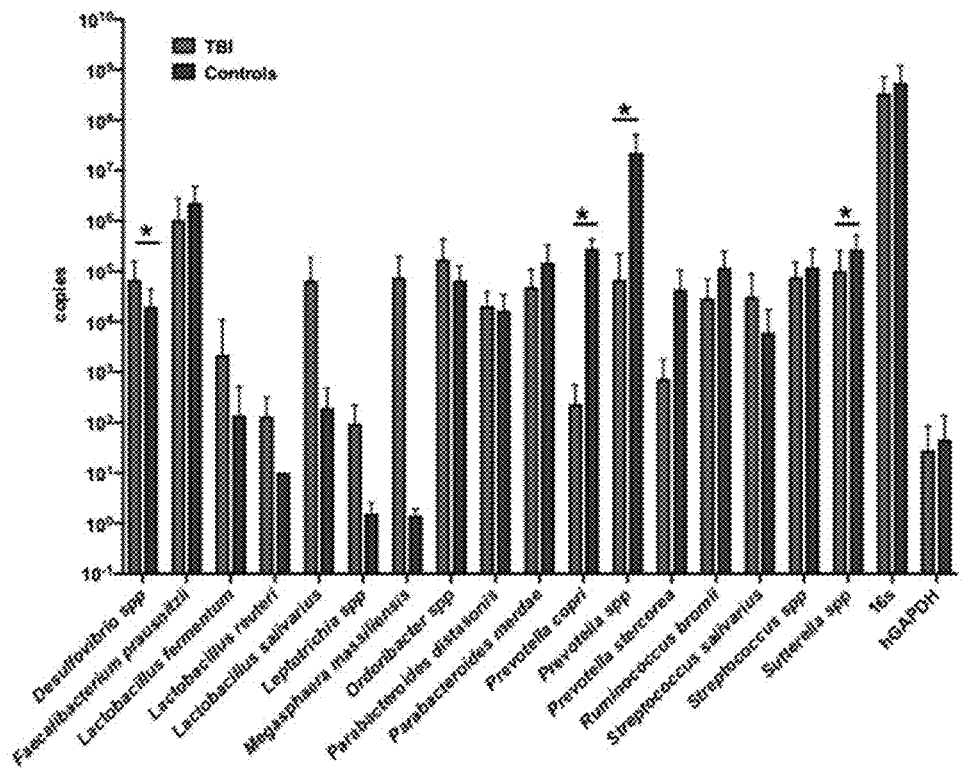

The consistency in the shifted TBI community structure was further confirmed by clustering analysis of qPCR data that provided absolute abundance (data are summarized in FIGS. 4A to 4C and Table 5). These data were produced from a novel qPCR array the inventors created based on the combined 16S rRNA and tuf gene NGS data as well as information from the literature. The array allowed simultaneous quantification of 94 bacterial (genus or species level), fungal and viral targets as well as quantification of both total 16S and human GAPDH (Table 5). Using this array, the inventors evaluated every DNA sample with sufficient quality allowing direct comparisons of the average absolute abundance profiles in TBI and control samples for these specific targets. This approach also provided accurate detection rates for each target across the samples. By this measure, there were no significant differences in average control 16S rRNA gene or human GAPDH copy numbers between the TBI and control cohorts (Table 5).

TABLE 5

Absolute abundance of selected bacterial targets based on qPCR analyses.

| TBI Array Primer | TBI Count | TBI Average | TBI SD | Controls Count | Controls Average | Controls SD | TBI fold change | P value |
|---|---|---|---|---|---|---|---|---|
| Akkermansia spp | 19 | 5.5E5 | 5.3E5 | 11 | 2.7E5 | 3.4E5 | 2.08 | 0.082 |
| Alistipes onderdonkii | 21 | 7.2E5 | 7.8E5 | 13 | 3.1E5 | 4.8E5 | 2.34 | 0.066 |
| Anaerotruncus colihominis | 22 | 5.8E3 | 7.5E3 | 15 | 4.8E3 | 1.1E4 | 1.21 | 0.762 |
| Bacteroides caccae | 13 | 4E4 | 4.8E4 | 14 | 7.8E4 | 6.3E4 | 0.51 | 0.087 |
| Bacteroides dorei | 13 | 5.1E4 | 8.7E4 | 7 | 5E4 | 7.9E4 | 1.03 | 0.969 |
| Bacteroides massiliensis | 6 | 1.6E3 | 1.7E3 | 8 | 3.2E3 | 4.7E3 | 0.51 | 0.407 |
| Bacteroides plebius | 2 | 4.6E2 | 1.5E2 | 4 | 3E5 | 4E5 | 0.002 | 0.233 |
| Bacteroides sartorii | 17 | 1E4 | 3.6E4 | 12 | 9.2E2 | 2E3 | 10.99 | 0.315 |
| Bacteroides stercoris | 12 | 1.5E5 | 2.6E5 | 10 | 9.9E4 | 1.8E5 | 1.56 | 0.561 |
| Bacteroides sterorirosoris | 14 | 9.4E4 | 3E5 | 9 | 5.9E2 | 1.2E3 | 158.53 | 0.261 |
| Bacteroides thetaiotoamicron | 15 | 2.8E4 | 3.6E4 | 10 | 6.2E3 | 1.4E4 | 4.57 | 0.044 |
| Bacteroides uniformis | 22 | 8.5E5 | 1.3E6 | 16 | 5.9E5 | 7.7E5 | 1.44 | 0.452 |
| Bacteroides vulgatus | 10 | 1.6E5 | 1.5E5 | 12 | 1.2E5 | 1.5E5 | 1.25 | 0.622 |
| Bifidobacterium bifidum | 7 | 1.4E5 | 1.4E5 | 3 | 3.6E5 | 1.4E5 | 0.39 | 0.082 |
| Clostridium leptum | 20 | 3E4 | 7E4 | 13 | 5.4E3 | 5.6E3 | 5.51 | 0.137 |
| Clostridium sybiosum | 22 | 3.1E3 | 5.3E3 | 14 | 1.5E3 | 3.1E3 | 2.13 | 0.247 |
| Collinsella spp | 21 | 1.1E6 | 9.7E5 | 16 | 1.3E6 | 1.7E6 | 0.89 | 0.759 |
| Desulfovibrio spp | 21 | 6.9E4 | 9E4 | 15 | 2E4 | 2.5E4 | 3.44 | 0.028 |
| Faecalibacterium prausnitzii | 22 | 1E6 | 1.7E6 | 16 | 2.3E6 | 2.5E6 | 0.45 | 0.097 |
| Lactobacillus fermentum | 17 | 2.2E3 | 8.9E3 | 11 | 1.4E2 | 3.9E2 | 15.58 | 0.357 |
| Lactobacillus reuteri | 5 | 1.3E2 | 1.8E2 | 1 | 10.1 | NA | 13.02 | NA |
| Lactobacillus salivarius | 8 | 6.6E4 | 1.2E5 | 4 | 1.9E2 | 2.9E2 | 341.34 | 0.171 |
| Leptotrichia spp | 2 | 95.5 | 1.3E2 | 2 | 1.6 | 1 | 61.22 | 0.485 |
| Megasphaera massiliensis | 4 | 7.6E4 | 1.2E5 | 2 | 1.43 | 1 | 53157.06 | 0.297 |
| Ordoribacter spp | 18 | 1.7E5 | 2.6E5 | 11 | 6.6E4 | 6.2E4 | 2.65 | 0.102 |
| Parabacteroides distasonis | 19 | 2.1E4 | 2E4 | 14 | 1.7E4 | 1.7E4 | 1.22 | 0.567 |
| Parabacteroides merdae | 18 | 4.9E4 | 5.9E4 | 14 | 1.5E5 | 1.9E5 | 0.33 | 0.072 |
| Prevotella copri | 2 | 2.3E2 | 3.3E2 | 9 | 2.8E5 | 1.5E5 | 0.001 | 0.001 |
| Prevotella spp | 19 | 6.9E4 | 1.5E5 | 16 | 2.2E7 | 3E7 | 0.003 | 0.009 |
| Prevotella stercorea | 2 | 7.4E2 | 1E3 | 2 | 4.4E4 | 6.2E4 | 0.02 | 0.505 |
| Ruminococcus bromii | 8 | 2.9E4 | 3.9E4 | 7 | 1.2E5 | 1.3E5 | 0.25 | 0.132 |
| Streptococcus salivarius | 22 | 3.1E4 | 5.9E4 | 15 | 6.1E3 | 1.1E4 | 5.13 | 0.066 |

TABLE 5-continued

Absolute abundance of selected bacterial targets based on qPCR analyses.

| TBI Array Primer | TBI | | | Controls | | | TBI fold change | P value |
|---|---|---|---|---|---|---|---|---|
| | Count | Average | SD | Count | Average | SD | | |
| *Streptococcus* spp | 22 | 7.7E4 | 7.5E4 | 16 | 1.2E5 | 1.6E5 | 0.64 | 0.314 |
| *Sutterella* spp | 22 | 1E5 | 1.6E5 | 16 | 2.7E5 | 2.6E5 | 0.37 | 0.026 |
| 16s | 22 | 3.4E8 | 3.7E8 | 15 | 5.5E8 | 6.6E8 | 0.63 | 0.299 |
| hGAPDH | 16 | 27.7 | 57.5 | 13 | 45.0 | 90.7 | 0.60 | 0.537 |

Clustering analysis of the absolute abundance data showed remarkable grouping of controls and TBI with some exceptions (e.g. 1BTW control and 2ATW and 6ATW TBI; FIG. 4A). There were no obvious characteristics in the available metadata (Table 1) that explained the unexpected clustering of these samples. From the 94 microbiome targets, the average abundance of targets identified as different by one of the previous methods, or found to be significantly different between the cohorts (multiple t test by the Holm-Sidak method, p<0.05), or to have greater than 10-fold differences between the cohorts were plotted (FIGS. 4B and 4C) and tabulated (Table 5).

PCR results indicated *Prevotella* spp were detected in 90% of the samples in each cohort with a 318-fold increase in absolute abundance in the control samples (p=0.009; Table 2). There were no significant differences in the *Lactobacillus* spp levels but *L. fermentum* and *L. salivarius* were substantially higher in titer in the TBI samples (average fold change of 15.6 and 341, respectively; FIGS. 4B and 4C and Table 6). Bacterial targets that had significantly higher absolute abundance in the TBI fecal samples and were commonly found in both cohorts included *Bacteroides sartorii* (11 fold), *B. sterorirosoris* (158 fold), *Clostridium leptum* (5.5 fold), *Streptococcus salivarius* (5.1 fold; Table 5). Two additional targets that were rarely detected but were substantially higher in TBI samples were *Leptotrichia* spp (61 fold) and *Megasphaera massiliensis* (53,000 fold). *Bacteroides plebius* (630 fold) and *Prevotella stercorea* (59 fold) were also rarely detected across both cohorts, but when present, were substantially higher in the control samples.

TABLE 6

Summary data from qPCR analyses

| TBI Array Primer | TBI | | | Controls | | | TBI fold change |
|---|---|---|---|---|---|---|---|
| | Count | Avg abundance | SD | Count | Avg abundance | SD | |
| *Akkermansia* spp | 19 | 5.5E5 | 5.3E5 | 11 | 2.7E5 | 3.4E5 | 2.08 |
| *Alistipes obesi* | 13 | 3.5E4 | 3.6E4 | 7 | 1.1E4 | 1.8E4 | 3.24 |
| *Alistipes onderdonkii* | 21 | 7.2E5 | 7.8E5 | 13 | 3.1E5 | 4.8E5 | 2.34 |
| *Alistipes putredinis* | 12 | 1.8E5 | 2.3E5 | 13 | 3.9E5 | 4.4E5 | 0.47 |
| *Alistipes shahii* | 13 | 1.1E4 | 1.7E4 | 9 | 9.9E3 | 9.7E3 | 1.13 |
| *Alloiococcus* spp | 22 | 2E5 | 2E5 | 16 | 1.7E5 | 1.3E5 | 1.20 |
| *Anaerotruncus colihominis* | 22 | 5.8E3 | 7.5E3 | 15 | 4.8E3 | 1.1E4 | 1.21 |
| *Bacteroides caccae* | 13 | 3.9E4 | 4.8E4 | 14 | 7.8E4 | 6.3E4 | 0.51 |
| *Bacteroides dorei* | 13 | 5.1E4 | 8.7E4 | 7 | 5E4 | 7.9E4 | 1.03 |
| *Bacteroides eggerthii* | 6 | 5.1E3 | 6.9E3 | 3 | 1.1E4 | 1.6E4 | 0.49 |
| *Bacteroides faecis* | 5 | 6.1E4 | 1.2E5 | 2 | 3.6E4 | 1.9E4 | 1.68 |
| *Bacteroides finegoldii* | 6 | 9.2E3 | 8.3E3 | 5 | 2.2E4 | 2.3E4 | 0.42 |
| *Bacteroides fragilis* | 12 | 5.6E4 | 1.4E5 | 5 | 9.9E3 | 1.5E4 | 5.62 |
| *Bacteroides massiliensis* | 6 | 1.6E3 | 1.7E3 | 8 | 3.2E3 | 4.7E3 | 0.51 |
| *Bacteroides nordii* | 8 | 4.4E3 | 6.3E3 | 4 | 8E3 | 1.5E4 | 0.55 |
| *Bacteroides ovatus* | 14 | 3.8E4 | 6.3E4 | 14 | 4.6E4 | 5.6E4 | 0.82 |
| *Bacteroides plebius* | 2 | 4.6E2 | 1.5E2 | 4 | 2.9E5 | 3.9E5 | 0.00 |
| *Bacteroides salyersiae* | 4 | 7.3E4 | 1.1E5 | 6 | 1.1E5 | 1.8E5 | 0.66 |
| *Bacteroides sartorii* | 17 | 1E4 | 3.6E4 | 12 | 9.2E2 | 2E3 | 10.99 |
| *Bacteroides stercoris* | 12 | 1.5E5 | 2.6E5 | 10 | 9.9E4 | 1.8E5 | 1.56 |
| *Bacteroides sterorirosoris* | 14 | 9.4E4 | 3E5 | 9 | 5.9E2 | 1.2E3 | 158.53 |
| *Bacteroides thetaiotoamicron* | 15 | 2.8E4 | 3.6E4 | 10 | 6.2E3 | 1.4E4 | 4.57 |
| *Bacteroides timonensis* | 15 | 4.6E4 | 1.1E5 | 11 | 1.6E4 | 2.6E4 | 2.91 |
| *Bacteroides uniformis* | 22 | 8.5E5 | 1.3E6 | 16 | 5.9E5 | 7.7E5 | 1.44 |
| *Bacteroides vulgatus* | 10 | 1.6E5 | 1.5E5 | 12 | 1.2E5 | 1.5E5 | 1.25 |
| *Bacteroides xylanisolvens* | 13 | 7.6E5 | 1.2E6 | 10 | 5.1E5 | 7.5E5 | 1.47 |
| *Bifidobacterium bifidum* | 7 | 1.4E5 | 1.4E5 | 3 | 3.6E5 | 1.4E5 | 0.39 |
| *Bifidobacterium longum* | 17 | 9.9E4 | 2E5 | 12 | 2.5E4 | 2.7E4 | 3.90 |
| *Bilophila wadsworthia* | 18 | 7.6E3 | 5.7E3 | 15 | 1.3E4 | 1.6E4 | 0.60 |
| *Blautia* spp | 22 | 1.5E7 | 1.9E7 | 16 | 9.2E6 | 7.2E6 | 1.57 |
| *Butyrivibrio* spp | 21 | 1.4E6 | 1.4E6 | 15 | 1.2E6 | 6.6E5 | 1.16 |
| *Candida albicans* | 6 | 4.4E2 | 6E2 | 2 | 1.6E2 | 38.3 | 2.80 |
| *Clostridium leptum* | 20 | 3E4 | 7E4 | 13 | 5.4E3 | 5.6E3 | 5.51 |
| *Clostridium sybiosum* | 22 | 3.1E3 | 5.3E3 | 14 | 1.5E3 | 3.1E3 | 2.13 |
| *Collinsella* spp | 21 | 1.1E6 | 9.7E5 | 16 | 1.3E6 | 1.7E6 | 0.89 |
| *Coprococcus comes* | 14 | 3.1E5 | 4E5 | 15 | 6.3E5 | 7E5 | 0.49 |

TABLE 6-continued

Summary data from qPCR analyses

| | TBI | | | Controls | | | |
|---|---|---|---|---|---|---|---|
| TBI Array Primer | Count | Avg abundance | SD | Count | Avg abundance | SD | TBI fold change |
| Cross-assembly phage (CPQ 56) | 12 | 8.5E5 | 1.2E6 | 5 | 1.5E6 | 3E6 | 0.55 |
| Cross-assembly phage (CPQ 64) | 10 | 5E6 | 4.6E6 | 4 | 8.1E6 | 1.3E7 | 0.62 |
| *Desulfovibrio* spp | 21 | 6.9E4 | 9E4 | 15 | 2E4 | 2.5E4 | 3.44 |
| *Dialister* spp | 22 | 1.1E5 | 1.3E5 | 16 | 3.7E5 | 7.9E5 | 0.30 |
| *Dorea* spp | 22 | 2.7E6 | 2.6E6 | 16 | 2.7E6 | 1.8E6 | 1.00 |
| *E. coli* | 10 | 6.3E3 | 1.6E4 | 9 | 9.3E4 | 2.7E5 | 0.07 |
| *Entercoccus* spp | 22 | 4.2E4 | 1.6E5 | 16 | 3E4 | 9.2E4 | 1.40 |
| *Enterococcus faecalis* | 10 | 1.8E2 | 5.1E2 | 4 | 3.6E2 | 4.2E2 | 0.50 |
| *Eubacterium rectale* | 16 | 5.3E5 | 1.1E6 | 15 | 9.4E5 | 1.1E6 | 0.56 |
| *Eubacterium siraeum* | 17 | 9.4E4 | 3.6E5 | 8 | 1.1E4 | 1.5E4 | 8.93 |
| *Eubacterium siraeum* | 15 | 2.2E2 | 3.8E2 | 5 | 5.9E3 | 1.3E4 | 0.04 |
| *Faecalibacterium prausnitzii* | 22 | 1E6 | 1.7E6 | 16 | 2.3E6 | 2.5E6 | 0.45 |
| *Fusobacterium nucleatum* | 17 | 83 | 2.8E2 | 12 | 33.2 | 76.2 | 2.51 |
| *Fusobacterium* spp | 20 | 6.6E2 | 2.1E3 | 16 | 3.6E2 | 7.2E2 | 1.83 |
| *Haemophilus* universal | 22 | 4.1E3 | 1E4 | 16 | 5.7E3 | 8.4E3 | 0.72 |
| *Holdemania filiformis* | 10 | 7E3 | 5.4E3 | 8 | 4.5E3 | 6.8E3 | 1.55 |
| *Lachnoclostridium* spp | 22 | 3.7E6 | 3E6 | 16 | 4.4E6 | 2.5E6 | 0.84 |
| *Lactobacillus fermentum* | 17 | 2.2E3 | 8.9E3 | 11 | 1.4E2 | 3.9E2 | 15.58 |
| *Lactobacillus rhamnosus* | 20 | 1.1E2 | 3.6E2 | 10 | 57.6 | 9.6E1 | 1.92 |
| *Lactobacillus salivarius* | 8 | 6.6E4 | 1.2E5 | 4 | 1.9E2 | 2.9E2 | 341.34 |
| *Lactobacillus* spp | 20 | 6.3E4 | 2.5E5 | 15 | 4.6E4 | 1.7E5 | 1.38 |
| *Lactococcus lactis* | 22 | 5.9E3 | 2E4 | 16 | 5.8E3 | 1.6E4 | 1.02 |
| *Megasphaera massiliensis* | 4 | 7.6E4 | 1.2E5 | 2 | 1.4 | 1 | 53157.06 |
| *Methanobrevibacter smithii* | 10 | 5.6E4 | 7.4E4 | 7 | 2.5E4 | 3.8E4 | 2.24 |
| *Ordoribacter* spp | 18 | 1.7E5 | 2.6E5 | 11 | 6.6E4 | 6.2E4 | 2.65 |
| *Parabacteroides distasonis* | 19 | 2.1E4 | 1.9E4 | 14 | 1.7E4 | 1.7E4 | 1.22 |
| *Parabacteroides merdae* | 18 | 4.9E4 | 5.9E4 | 14 | 1.5E5 | 1.9E5 | 0.33 |
| *Parasutterella excrementihominis* | 10 | 3.3E3 | 6.5E3 | 12 | 2.5E3 | 3.9E3 | 1.32 |
| *Prevotella copri* | 2 | 2.3E2 | 3.3E2 | 9 | 2.8E5 | 1.5E5 | 0.00 |
| *Prevotella corporis* | 6 | 5.4E2 | 9.6E2 | 5 | 1E2 | 1.3E2 | 5.40 |
| *Prevotella disiens* | 5 | 1.3E2 | 1.1E2 | 3 | 29.7 | 34.1 | 4.52 |
| *Prevotella* spp | 19 | 6.9E4 | 1.5E5 | 16 | 2.2E7 | 3E7 | 0.002 |
| *Prevotella stercorea* | 2 | 7.4E2 | 1E3 | 8 | 4.4E4 | 6.2E4 | 0.02 |
| *Pseudoflavonifractor capillosus* | 21 | 2E3 | 2.6E3 | 16 | 2.6E3 | 3.6E3 | 0.77 |
| *Ruminococcus bicirculans* | 13 | 5E5 | 5.1E5 | 8 | 4.6E5 | 7E5 | 1.08 |
| *Ruminococcus bromii* | 8 | 2.9E4 | 3.9E4 | 7 | 1.2E5 | 1.3E5 | 0.25 |
| *Ruminococcus obeum* | 14 | 6.9E4 | 7.1E4 | 15 | 5.7E4 | 7.7E4 | 1.21 |
| *Ruminococcus torques* | 21 | 2.3E3 | 5.3E3 | 13 | 2.7E2 | 5.2E2 | 8.58 |
| *Streptococcus salivarius* | 22 | 3.1E4 | 5.9E4 | 15 | 6.1E3 | 1.1E4 | 5.13 |
| *Streptococcus* spp | 22 | 7.7E4 | 7.5E4 | 16 | 1.2E5 | 1.6E5 | 0.64 |
| *Subdoligranulum* spp | 19 | 6.2E4 | 9.7E4 | 13 | 7.6E4 | 1.2E5 | 0.81 |
| Sulfate-reducing Bacteria - DSCR1 | 20 | 2E4 | 2.1E4 | 15 | 1.7E4 | 1.6E4 | 1.17 |
| *Sutterella* spp | 22 | 1E5 | 1.6E5 | 16 | 2.7E5 | 2.6E5 | 0.37 |
| *Veillonella* spp | 22 | 2.4E3 | 4.3E3 | 14 | 2.4E4 | 6.1E4 | 0.10 |
| 16s | 22 | 3.4E8 | 3.7E8 | 15 | 5.5E8 | 6.6E8 | 0.63 |
| hGAPDH | 16 | 27.7 | 5.8E1 | 13 | 45.9 | 90.7 | 0.60 |

Correlations between specific microbes and amino acid levels and biosynthesis potential. The inventors previously reported one of the long-term impacts of moderate/severe TBI was altered amino acid levels post-meal[2]. Such alterations could lead to or be caused by altered mucosal microenvironments contributing to the creation and/or maintenance of a shifted microbiome. Subjects in both cohorts were asked to fast and then were provided a standardized meal followed by a blood draw 90 minutes after the meal was consumed. Consistent with the previous report, the TBI patients had significant reductions in the concentration of a number of amino acids as shown in Table 7. These data were correlated with the metagenomic data to reveal a positive correlation between the relative abundance of *Prevotella* spp. and all amino acids.

The present invention includes providing or eliminating from the gut flora of a TBI patient one or more of the bacterial listed in Tables 3, 4, 5 and/or 6, as the case may be, to bring the gut flora to alignment with a normal gut flora. For example, if the bacteria are listed as being found in higher amounts in TBI patients, then those bacteria can be eliminated from the gut flora. Conversely, if the TBI patient lacks certain bacteria (or have a low relative presence of the bacteria in their gut flora), then the gut flora can be supplemented with the missing or reduced bacteria to, again, bring them toward a more normal distribution of flora found in normal individuals (subject that do not have TBI and/or another disease or condition).

TABLE 7

Serum Amino Acid Concentrations in TBI and control cohorts following a standardized meal.

| Amino Acid | TBI Avg | TBI SDEV | Control Avg | Control SDEV | P value |
|---|---|---|---|---|---|
| L-Threonine | 81.8 | 23.23 | 104.2 | 35.41 | 0.021 |
| L-Tryptophan | 36.3 | 13.54 | 50.6 | 13.59 | 0.002 |
| L-Methionine | 17.0 | 4.32 | 19.8 | 5.11 | 0.065 |
| 1-Methyl-L-histidine | 6.8 | 4.31 | 9.7 | 6.45 | 0.093 |
| L-a-Amino-n-butyric Acid | 10.0 | 2.67 | 13.2 | 5.01 | 0.014 |
| L-alpha-Aminoadipic Acid | 0.7 | 0.52 | 1.1 | 0.75 | 0.093 |
| L-Sarcosine | 34.1 | 30.17 | 56.1 | 27.74 | 0.023 |
| tryptophan/LNAA | 0.06 | 0.02 | 0.08 | 0.02 | 0.068 |
| tryptophan/BCAA | 0.12 | 0.04 | 0.15 | 0.04 | 0.063 |

Values shown are concentration in uM except for the last two rows that show the ratio of the indicated amino acids for each cohort. P value was calculated by a Student's T test with p<0.05 considered significant as indicated by bolded text.

Figure 5:
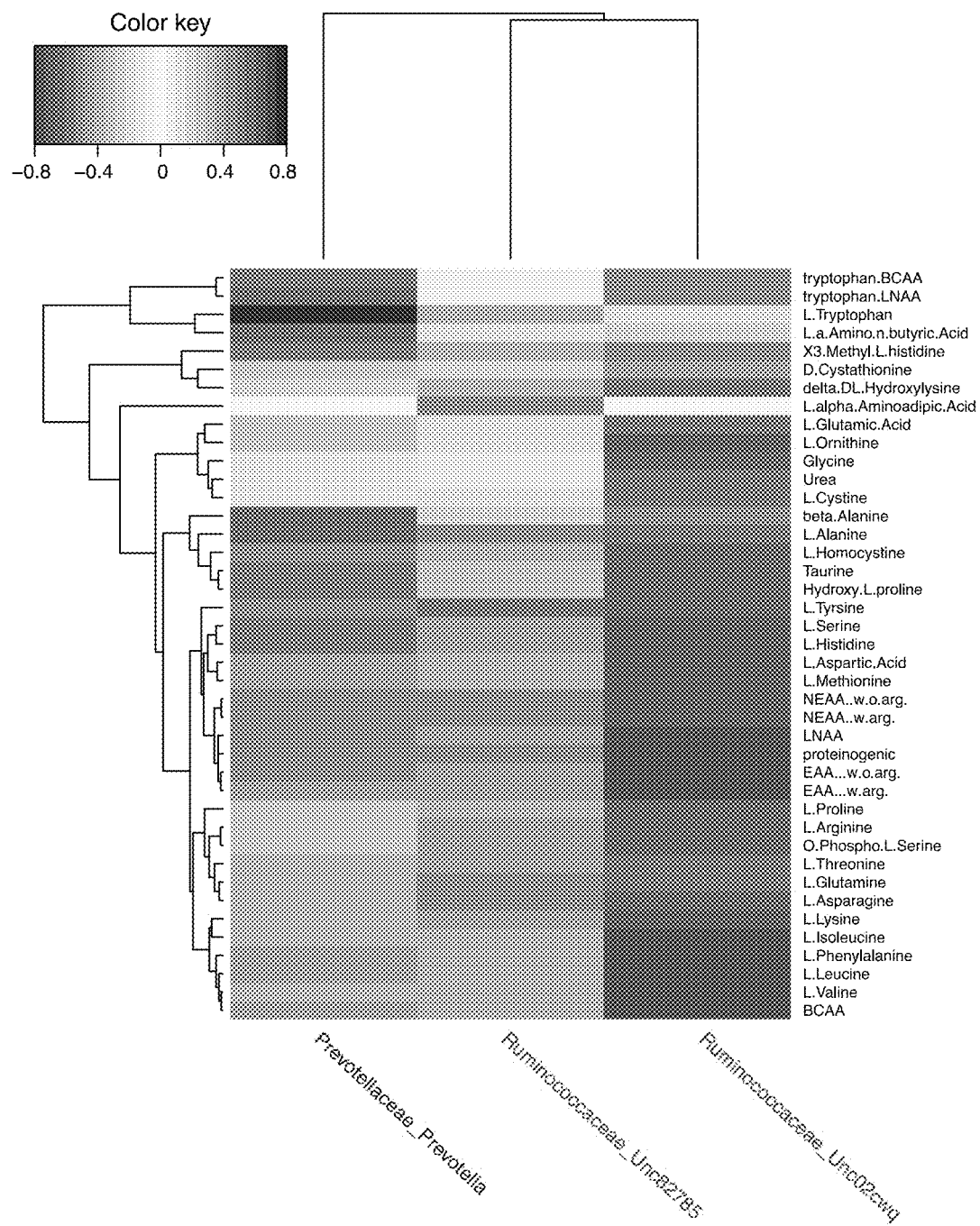
FIG. 5 shows a heat map associating amino acid concentrations with bacterial relative abundance. Using MixOmics[32] implemented in R [v3.3;[30]] correlations between the bacterial relative abundance and the concentration of selected amino acids was completed using sparse partial least squares regression (sPLS) performed in canonical mode with LASSO penalization. The results for 2 *Ruminococcaceae* spp. and *Prevotella* spp. are presented as a heat map.

In contrast, the relative abundance of the two unclassified *Ruminococcaceae* spp. were generally negatively correlated with relative levels of the amino acids. Tryptophan:BCAA ratio, tryptophan:LNAA ratio, L-tryptophan, B-alanine and alanine showed the strongest positive correlations with *Prevotella* (FIG. 5). Using the one minus Pearson correlation algorithm for the absolute quantities (FIG. 4) the inventors eliminated those samples that failed to group with the proper cohort producing a data set with those samples that clustered exclusively to control or TBI cohorts (most similar to the average group profile). Similar statistical differences were identified for both L-Tryptophan (Control, 1.67 vs TBI, 1.54; p=0.025) and also for L-Sarcosine (Control, 1.66 vs TBI, 1.00; p=0.029) by unpaired t testing, corroborating the metagenomic correlations.

Metagenomic data from individual samples also were used to identify KEGG modules related to amino acid metabolism and fatty acid biosynthesis (summarized in Table 8). The results showed that the *Akkermansia, Bacteroides* and *Streptococcus* genera as well as a number of unclassified metagenomes that were more abundant in TBI samples, carried significantly higher levels of amino acid biosynthesis capabilities relative to the control samples (Table 8). Although not significant, the presence of *Roseburia* contributed to the overabundance of amino acid biosynthetic pathways in the TBI samples. The *Bacteroides* levels were of mixed results between the cohorts similar to the NGS and PCR results showing specific species were associated with TBI or controls. At the *Bacteroides* genus level, control communities carried significantly higher levels of biosynthetic machinery for isoleucine, leucine, lysine and serine (Table 8). Considering the compiled KEGG module data, metabolic machinery for cysteine, histidine, isoleucine, leucine, lysine, methionine, ornithine, proline, serine, tryptophan, tyrosine and valine were identified as more abundant in the TBI fecal communities compared to controls. Because of the potent signaling and neurological functions of short chain fatty acids the inventors also noted that *Akkermansia, Roseburia* and unclassified metagenomes also significantly increased the machinery for initiation and elongation of fatty acids (Table 8).

TABLE 8

KEGG pathway modules identified as significantly over or under represented in TBI fecal samples compared to the control cohort.

| KEGG Module | Description | Genus | Control AVG (SEM) | TBI AVG (SEM) | Control Detect n = 16 | TBI Detect n = 20 | T-test |
|---|---|---|---|---|---|---|---|
| M00021 | Cysteine biosynthesis, serine => cysteine | Streptococcus | 54 (23) | 198 (52) | 19% | 65% | 0.024 |
|  |  | Metagenome | 11 (3) | 23 (5) | 81% | 60% | 0.046 |
| M00026 | Histidine biosynthesis, PRPP => histidine | Metagenome | 18158 (1780) | 26413 (2367) | 100% | 100% | 0.009 |
| M00570 | Isoleucine biosynthesis, threonine => 2-oxobutanoate => isoleucine | Akkermansia | 470 (189) | 2001 (641) | 44% | 70% | 0.036 |
|  |  | Metagenome | 19510 (2088) | 27425 (2194) | 100% | 100% | 0.013 |
| M00535 | Isoleucine biosynthesis, pyruvate => 2-oxobutanoate | Akkermansia | 101 (40) | 536 (169) | 56% | 70% | 0.025 |
|  |  | Bacteroides | 266 (93) | 31 (7) | 56% | 20% | 0.035 |
| M00432 | Leucine biosynthesis, 2-oxoisovalerate => 2-oxoisocaproate | Akkermansia | 193 (82) | 1078 (323) | 56% | 70% | 0.018 |
|  |  | Bacteroides | 265 (93) | 37 (18) | 56% | 10% | 0.04 |
|  |  | Metagenome | 10063 (978) | 14103 (1485) | 100% | 100% | 0.03 |
| M00016 | Lysine biosynthesis, succinyl-DAP pathway, aspartate => lysine | Akkermansia | 277 (121) | 1278 (443) | 38% | 60% | 0.049 |
|  |  | Bacteroides | 775 (218) | 77 (31) | 31% | 10% | 0.032 |
| M00525 | Lysine biosynthesis, acetyl-DAP pathway, aspartate => lysine | Akkermansia | 277 (121) | 1278 (443) | 38% | 60% | 0.049 |
|  |  | Bacteroides | 775 (218) | 77 (31) | 31% | 10% | 0.032 |
| M00526 | Lysine biosynthesis, DAP dehydrogenase pathway, aspartate => lysine | Akkermansia | 279 (111) | 1216 (409) | 44% | 70% | 0.043 |
|  |  | Bacteroides | 775 (218) | 77 (31) | 31% | 10% | 0.032 |
| M00527 | Lysine biosynthesis, DAP aminotransferase pathway, aspartate => lysine | Bacteroides | 754 (281) | 281 (24) | 69% | 25% | 0.036 |
| M00035 | Methionine degradation | Metagenome | 5677 (435) | 8174 (900) | 100% | 100% | 0.019 |
| M00028 | Ornithine biosynthesis, glutamate => ornithine | Akkermansia | 286 (123) | 1297 (408) | 50% | 70% | 0.031 |
|  |  | Metagenome | 11665 (1164) | 15684 (1530) | 100% | 100% | 0.044 |
| M00015 | Proline biosynthesis, glutamate => proline | Akkermansia | 54 (27) | 267 (80) | 50% | 70% | 0.023 |
|  |  | Streptococcus | 49 (23) | 186 (57) | 31% | 65% | 0.042 |

TABLE 8-continued

KEGG pathway modules identified as significantly over or under represented in TBI fecal samples compared to the control cohort.

| KEGG Module | Description | Genus | Control AVG (SEM) | TBI AVG (SEM) | Control Detect n = 16 | TBI Detect n = 20 | T-test |
|---|---|---|---|---|---|---|---|
| M00020 | Serine biosynthesis, glycerate-3P => serine | Bacteroides | 7 (1) | 3 (1) | 13% | 10% | 0.03 |
| | | Metagenome | 17 (3) | 51 (12) | 56% | 60% | 0.018 |
| M00023 | Tryptophan biosynthesis, chorismate =>tryptophan | Akkermansia | 366 (165) | 1841 (609) | 50% | 70% | 0.034 |
| | | Bacteroides | 257 (236) | 1353 (374) | 13% | 40% | 0.045 |
| | | Metagenome | 12547 (1222) | 18751 (2119) | 100% | 100% | 0.017 |
| M00025 | Tyrosine biosynthesis, chorismate => tyrosine | Metagenome | 4013 (710) | 6488 (941) | 69% | 85% | 0.046 |
| M00019 | Valine/isoleucine biosynthesis, pyruvate => valine/2-oxobutanoate => isoleucine | Metagenome | 17117 (1793) | 24016 (2010) | 100% | 100% | 0.015 |
| M00083.3 | Fatty acid biosynthesis, elongation | Akkermansia | 256 (99) | 1140 (325) | 50% | 70% | 0.02 |
| | | Roseburia | 134 (46) | 594 (201) | 69% | 70% | 0.04 |
| M00082 | Fatty acid biosynthesis, initiation | Metagenome | 9967 (801) | 14390 (1763) | 100% | 100% | 0.03 |

Patients with chronic traumatic brain injury (TBI) requiring long-term, permanent care suffer a complex and varied set of clinical symptoms and comorbidities that persist for many years beyond the acute brain injury including hypoaminoacidemia and altered pituitary function. The results from this novel, two-site, clinical investigation unequivocally illustrates that chronic TBI patients exhibit different fecal microbiome community structures compared to controls. These differences persisted and became more defined after rigorous secondary targeted analyses in combination with group stratification and confound removal. The absence or reduction of *Prevotella* spp. and *Bacteroidies* spp., and higher abundance of *Ruminococcaceae* spp. in chronic TBI compared to controls offers immediate therapeutic targets for further investigation in minimizing patient morbidity.

Notably, these results demonstrate that altered bacterial communities directly affect TBI. By way of explanation, and not a limitation of the present invention, these shifts in community structure are likely created and maintained by and also contribute to an altered intestinal mucosa that creates a selective microenvironment in a perpetuating cycle.

The decreased post-meal amino acid levels of the TBI patients in the cohorts show that the intestinal microenvironment would also have altered amino acid metabolism. Varied abundance of *Prevotella copri* and *Bacteroides vulgatus* have previously been associated with increased serum amino acid concentrations especially the branch chain amino acids[35]. The present findings show that *P. copri* was the most abundant *Prevotella* in the control cohort but this species was significantly reduced or absent in the participants with TBI. However, *B. vulgatus* was relatively uncommon in the cohorts and, when present, was more abundant in the TBI samples. Bacteria in the *Ruminococcaceae* family have been previously associated with amino acid deficient microenvironments[36] and were higher in the fecal samples from TBI patients in the cohort. KEGG analyses, confirmed that the bacterial shifts occurring in TBI patients encoded higher levels of necessary machinery for biosynthesis of several amino acids. These community shifts also may contribute to altered inflammation that was detected and, through production of different metabolites including short chain fatty acids, would further disrupt normal function of the autonomic nerves (e.g. vagal) altering intestinal contractility[37-39]. Reduced gut motility also disturbs the microflora balance and promotes small intestinal bacterial overgrowth contributing to dysbiosis[40]. The present invention proves that the process based on the combined results in these two geographically distinct cohorts and emphasizes the need for careful cellular and molecular analyses of the TBI intestinal mucosa for treatment.

These studies were completed in individuals that suffered moderate to severe TBI leading to disabilities requiring full-time supportive care. To address the impact of residence in a care facility the inventors recruited from two distinct communities that offered distinct lifestyles and diets. Even in the small TBI cohorts from the two locations the inventors identified significant changes in specific organisms that were supported and confirmed through multiple NGS approaches and subsequent qPCR analyses. The fecal microbiome profiles the inventors obtained from the controls were typical of healthy communities with greater diversity than was observed in the TBI samples[12,13]. Stratification of the data using participant metadata did not reveal any obvious confounder beyond TBI. Importantly, the lack of distinction between the two geographic sites where different food, environment and even medication approaches demonstrate the differences between the control and TBI cohorts. The inventors' rigorous approaches, each confirming the last, have identified a number biomarker organisms in fecal samples with altered abundance supporting the development of targeted qPCR panels for less expensive, higher throughput analyses of larger cohorts that are now being performed.

Consistent with other chronic inflammatory conditions including obesity, the fecal microbiome of chronic TBI patients demonstrated higher abundance of *Firmicutes* and decreased abundance of Bacteriodetes compared to controls. Within the Bacteroidetes phylum, TBI fecal communities showed a loss of *Prevotella* spp. compared to controls. Despite the development and utilization of a tuf gene targeted NGS approach the inventors were unable to account for all of the detected *Prevotella* sequences at the species level. By several approaches it was clear that *Prevotella* spp. were very common in both cohorts (over 90% of the individual samples were positive) but the *P. copri* and *P. stercorea* species that showed significantly lower abundance in TBI samples were not as common. Interestingly, expansion of *P. copri* and *P. stercorea* in microbiome communities has been associated with localized systemic disease including periodontitis, rheumatoid arthritis, bacterial vaginosis and other chronic inflammatory conditions[41]. By way of explanation, and in no way a limitation of the present invention, it is suggested that, mechanistically, overly abundant *Prevotella* spp. have been linked to function of T helper type 17 (Th17) cells that can be directly causative for types of inflammation[42]. Studies of individuals with non-alcoholic fatty liver disease have suggested that *Prevotella* spp. is also significantly reduced relative to controls[43]. This same study also identified that the *Alistipes* genus was significantly reduced while *Anaerobacter* and *Streptococcus* genera were increased. The group concluded that such community changes led to alterations in microvilli and intestinal barrier integrity (caused by reductions of tight junctions) consistent with impacts on GI function[43].

Similar disruption of intestinal integrity has been described for TBI outcomes, but the mechanisms remain unknown. Following TBI in animal models and in some clinical studies, expression of proteins associated with tight junctions including ZO-1 and occludin are significantly decreased as are anatomical aspects of the GI tract[11]. Short-term evaluations of the intestinal microbiome following TBI showed quick changes in the community profiles in experimental animals. The inventors' findings are the first to examine and report the long-term outcomes of TBI on human intestinal communities including impacts on amino acid levels and chronic inflammation[2].

The inventors observed a significant increase in abundance of *Ruminococcaceae* spp. in TBI patients that were, on average, 20 years post-injury. Although total *Bacteroides* spp. was higher in the controls, thorough tuf gene analysis and subsequent species-specific PCR approaches clarified that some specific *Bacteroides* species were more abundant in TBI fecal communities. Specifically, three very commonly detected *Bacteroides* genus members, *B. uniformis* (detected in all fecal samples), *B. stercoris* and *B. thetaiotaomicron* (both found in more than half of all samples) were more abundant in TBI by both tuf gene and qPCR analyses.

Finally, the PCR analyses also revealed that *Sutterella* spp., that were detected in every sample, were significantly less abundant in TBI samples than controls. Recent work with microbiomes transplanted from patients with multiple sclerosis (MS) to mice confirmed decreased *Sutterella* spp. was associated with MS[46]. In previous studies, higher *Sutterella* spp. was associated with reduced development of autoimmune encephalomyelitis in mice[47] and better outcomes for individuals with inflammatory bowel disease[48]. However, a recent study involving human fecal microbiome transplant (FMT) treating ulcerative colitis indicated that enrichment of *Sutterella wadsworthensis* was associated with poor treatment outcomes[49]. In this same study *Roseburia inulivorans* was positively associated with successful FMT treatment in concert with increased short chain fatty acid synthesis[49].

Utilizing the reconstruction of metabolic pathways from metagenomic data, the relative abundance of specific metabolic pathways was evaluated based on the composition of fecal microbiota communities. These data illustrated the selection of bacterial communities that had greater capability of biosynthesis of selected amino acids. In addition to critical essential amino acids, sequences encoding synthesis machinery for a number of non-essential amino acids were significantly more abundant in the TBI samples. Fewer KEGG modules related to fatty acid biosynthesis were significantly associated, but it is notable that the *Akkermansia* spp. and *Roseburia* spp. also led to increased fatty acid biosynthesis capability in the TBI communities.

The data generated in this novel, two-site human clinical study involving chronic TBI and control subjects demonstrates an altered intestinal mucosa lacking available amino acids and fatty acids leading to enrichment of bacterial types that carry the necessary metabolic machinery to address this deficit. Although postprandial nutritional absorption influences GH secretion, the nutrients responsible for regulating this secretion are not clear[50]. The enterocytes lining the small intestinal tract have rapid turnover and are highly metabolic, scavenging a large proportion of dietary amino acids. These results show that the chronic and long-lasting effects in these TBI patients are not quickly overcome and can lead to comorbidities long after the initial injury. The hypoaminoacidemia observed in TBI patients helps explain the subsequent reduction in growth hormone function and other pituitary issues seen in many TBI patients. Thus, these results demonstrate that the injury-based disruption of intestinal metabolism in TBI patients, in addition to alterations in nutrient utilization by the microbiota, likely contributed to the altered amino acid profiles observed by the present inventors in TBI patients[2]. The cascade of sequelae can be targeted with multiple treatment methods, including fecal microbiota transplant (FMT), oral microbiota transplant, colonoscope microbiota transplant, and the like.

Thus, the inventors identified novel, therapeutically relevant biomarkers that can be used to treat symptomatic, chronic TBI patients, and offering clinically meaningful treatment options for TBI-related comorbidities. Given the complexity of the impact on both the brain, CNS, immune, metabolic, inflammatory, pituitary, and intestinal microbiome, the results herein yielded both therapeutic and mechanistic insights into TBI. Notably, the results show that supplementation or replacement of the dysbiotic intestinal community via, e.g., fecal microbiota transplant (FMT) can be used to treat TBI patients and its associated comorbidities.

The present invention can be provided in a wide variety of modalities. For example, the patient can be given a bacterial composition that modified the flora about from the TBI flora to a normal flora, before, during, or after undergoing a colon cleanse treatment. In one example, the bacterial composition can be delivered to the patient by colonoscope. Further, the bacterial composition does not necessarily need to come from a fecal transplant, rather, the bacteria can be lab grown and even customized to address specific needs of the patient.

The inventors of the present invention sought to determine whether specific gut microbiota and/or microbial metabolites are associated with brain injury associated fatigue and/or altered cognition.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Taylor, C. A., Bell, J. M., Breiding, M. J. & Xu, L. Traumatic Brain Injury-Related Emergency Department Visits, Hospitalizations, and Deaths—United States, 2007 and 2013. MMWR. Surveill. Summ. 66, 1-16 (2017).
2. Durham, W. J. et al. Hypoaminoacidemia Characterizes Chronic Traumatic Brain Injury. J. Neurotrauma 34, 385-390 (2017).
3. Yamamoto, S., DeWitt, D. S. & Prough, D. S. Impact & Blast Traumatic Brain Injury: Implications for Therapy. Molecules 23, 245 (2018).
4. Rogers, G. B. et al. From gut dysbiosis to altered brain function and mental illness: mechanisms and pathways. Mol. Psychiatry 21, 738-748 (2016).
5. Sun, M.-F. & Shen, Y.-Q. Dysbiosis of gut microbiota and microbial metabolites in Parkinson's Disease. Ageing Res. Rev. 45, 53-61 (2018).
6. Duvallet, C., Gibbons, S. M., Gurry, T., Irizarry, R. A. & Alm, E. J. Meta-analysis of gut microbiome studies identifies disease-specific and shared responses. Nat. Commun. 8, 1784 (2017).
7. Winter, G., Hart, R. A., Charlesworth, R. P. G. & Sharpley, C. F. Gut microbiome and depression: what we know and what we need to know. Rev. Neurosci. 29, 629-643 (2018).
8. Mayer, E. A., Tillisch, K. & Gupta, A. Gut/brain axis and the microbiota. J. Clin. Invest. 125, 926-38 (2015).
9. Sundman, M. H., Chen, N.-K., Subbian, V. & Chou, Y.-H. The bidirectional gut-brain-microbiota axis as a potential *nexus* between traumatic brain injury, inflammation, and disease. Brain. Behav. Immun. 66, 31-44 (2017).
10. Martin, C. R. & Mayer, E. A. Gut-Brain Axis and Behavior. Nestle Nutr. Inst. Workshop Ser. 88, 45-53 (2017).
11. Zhu, C. S., Grandhi, R., Patterson, T. T. & Nicholson, S. E. A review of traumatic brain injury and the gut microbiome: Insights into novel mechanisms of secondary brain injury and promising targets for neuroprotection. Brain Sciences (2018). doi:10.3390/brainsci8060113
12. Turnbaugh, P. J. et al. The Human Microbiome Project. Nature 449, 804-810 (2007).

13. Gill, S. R. et al. Metagenomic Analysis of the Human Distal Gut Microbiome. Science (80-.). 312, 1355-1359 (2006).
14. Bansal, V. et al. Stimulating the central nervous system to prevent intestinal dysfunction after traumatic brain injury. J. Trauma 68, 1059-64 (2010).
15. Katzenberger, R. J., Ganetzky, B. & Wassarman, D. A. The gut reaction to traumatic brain injury. Fly (Austin). 9, 68-74 (2015).
16. Human, T. et al. A framework for human microbiome research. Nature 486, 207-214 (2012).
17. Human, T. & Project, M. Structure, function and diversity of the healthy human microbiome. Nature 486, 207-14 (2012).
18. Caporaso, J. G. et al. Ultra-high-throughput microbial community analysis on the Illumina HiSeq and MiSeq platforms. ISME J. 6, 1621-4 (2012).
19. Edgar, R. C. Search and clustering orders of magnitude faster than BLAST. Bioinformatics 26, 2460-1 (2010).
20. Edgar, R. C. UPARSE: highly accurate OTU sequences from microbial amplicon reads. Nat. Methods 10, 996-8 (2013).
21. Quast, C. et al. The SILVA ribosomal RNA gene database project: improved data processing and web-based tools. Nucleic Acids Res. 41, D590-6 (2013).
22. Martin, M. Cutadapt removes adapter sequences from high-throughput sequencing reads. EMBnet.journal 17, 10-12 (2011).
23. Schmieder, R. & Edwards, R. Quality control and preprocessing of metagenomic datasets. Bioinformatics 27, 863-864 (2011).
24. Langmead, B. & Salzberg, S. L. Fast gapped-read alignment with Bowtie 2. Nat Methods 9, 357-359 (2012).
25. Ye, Y. & Doak, T. G. A Parsimony Approach to Biological Pathway Reconstruction/Inference for Genomes and Metagenomes. PLoS Comput. Biol. 5, e1000465 (2009).
26. Klindworth, A. et al. Evaluation of general 16S ribosomal RNA gene PCR primers for classical and next-generation sequencing-based diversity studies. Nucleic Acids Res. (2013). doi:10.1093/nar/gks808
27. Blankenberg, D. et al. Manipulation of FASTQ data with galaxy. Bioinformatics (2010). doi:10.1093/bioinformatics/btq281
28. Yilmaz, P. et al. The SILVA and 'all-species Living Tree Project (LTP)' taxonomic frameworks. Nucleic Acids Res. (2014). doi:10.1093/nar/gkt1209
29. Lozupone, C. & Knight, R. UniFrac: a new phylogenetic method for comparing microbial communities. Appl. Environ. Microbiol. 71, 8228-35 (2005).
30. Team, R. C. R: A language and environment for statistical computing. (2014).
31. Benjamini, Y. & Hochberg, Y. Controlling the False Discovery Rate: A Practical and Powerful Approach to Multiple Testing. J. R. Stat. Soc. Ser. B 57, 289-300 (1995).
32. Lê Cao, K.-A., Gonzalez, I. & Déjean, S. integrOmics: an R package to unravel relationships between two omics datasets. Bioinformatics 25, 2855-6 (2009).
33. Lê Cao, K.-A., Rossouw, D., Robert-Granié, C. & Besse, P. A sparse PLS for variable selection when integrating omics data. Stat. Appl. Genet. Mol. Biol. 7, Article 35 (2008).
34. Grimes, L. et al. Intraluminal Flagellin Differentially Contributes to Gut Dysbiosis and Systemic Inflammation following Burn Injury. PLoS One 11, e0166770 (2016).
35. Pedersen, H. K. et al. Human gut microbes impact host serum metabolome and insulin sensitivity. Nature 535, 376-381 (2016).
36. Herbeck, J. L. & Bryant, M. P. Nutritional features of the intestinal anaerobe *Ruminococcus bromii*. Appl. Microbiol. 28, 1018-22 (1974).
37. Olsen, A. B. et al. Effects of traumatic brain injury on intestinal contractility. Neurogastroenterol. Motil. 25, 593-e463 (2013).
38. Smith, K. TBI affects intestinal motility. Nat. Rev. Gastroenterol. Hepatol. 10, 260 (2013).
39. Esterov, D. & Greenwald, B. D. Autonomic Dysfunction after Mild Traumatic Brain Injury. Brain Sci. 7, 100 (2017).
40. Roland, B. C. et al. Small Intestinal Transit Time Is Delayed in Small Intestinal Bacterial Overgrowth. J. Clin. Gastroenterol. 49, 571-6 (2015).
41. Pianta, A. et al. Evidence of the Immune Relevance of *Prevotella copri*, a Gut Microbe, in Patients With Rheumatoid Arthritis. Arthritis Rheumatol. 69, 964-975 (2017).
42. Larsen, J. M. The immune response to *Prevotella* bacteria in chronic inflammatory disease. Immunology (2017). doi:10.1111/imm.12760
43. Jiang, W. et al. Dysbiosis gut microbiota associated with inflammation and impaired mucosal immune function in intestine of humans with non-alcoholic fatty liver disease. Sci. Rep. 5, 8096 (2015).
44. Javurek, A. B. et al. Gut Dysbiosis and Neurobehavioral Alterations in Rats Exposed to Silver Nanoparticles. Sci. Rep. 7, 2822 (2017).
45. Nagy-Szakal, D. et al. Fecal metagenomic profiles in subgroups of patients with myalgic encephalomyelitis/chronic fatigue syndrome. Microbiome 5, 44 (2017).
46. Berer, K. et al. Gut microbiota from multiple sclerosis patients enables spontaneous autoimmune encephalomyelitis in mice. Proc. Natl. Acad. Sci. U.S.A 114, 10719-10724 (2017).
47. Miller, P. G., Bonn, M. B., Franklin, C. L., Ericsson, A. C. & McKarns, S. C. TNFR2 Deficiency Acts in Concert with Gut Microbiota To Precipitate Spontaneous Sex-Biased Central Nervous System Demyelinating Autoimmune Disease. J. Immunol. 195, 4668-84 (2015).
48. Morgan, B. P. & Harris, C. L. Complement, a target for therapy in inflammatory and degenerative diseases. Nat. Rev. Drug Discov. 14, 857-877 (2015).
49. Paramsothy, S. et al. Specific Bacteria and Metabolites Associated With Response to Fecal Microbiota Transplantation in Patients With Ulcerative Colitis. Gastroenterology (2018). doi:10.1053/j.gastro.2018.12.001
50. Smeets, E. T. H. C., Schutzler, S. E., Wei, J. Y., Azhar, G. & Wolfe, R. R. Do anabolic nutritional supplements stimulate human growth hormone secretion in elderly women with heart failure? Physiol. Rep. 5, e13366 (2017).

What is claimed is:

1. A composition for treating brain injury associated fatigue or altered cognition in a human patient comprising one or more probiotic bacteria selected from at least one of: *Prevotella* spp or *Bacteroidies* spp, in an effective amount sufficient to reduce or eliminate the brain injury associated fatigue or altered cognition and an agent that reduces or eliminates *Ruminococcaceae* genus bacteria, wherein the agent that reduces or eliminates *Ruminococcaceae* genus bacteria is selected from an amino acid mixture, an antibacterial agent, a bacteriophage, or an antimicrobial CRISP-Cas system agent.

2. The composition of claim 1, wherein the composition further comprises a fecal transplant comprising *Prevotella* spp or *Bacteroidies* spp.

3. The composition of claim 1, wherein the composition further comprises an amino acid mixture that promotes the growth of *Prevotella* spp or *Bacteroidies* spp.

* * * * *